United States Patent [19]

Thomas et al.

[11] Patent Number: 5,312,911
[45] Date of Patent: May 17, 1994

[54] CYSTEINE-MODIFIED ACIDIC FIBROBLAST GROWTH FACTOR

[75] Inventors: Kenneth A. Thomas, Chatham Burough; David L. Linemeyer, Westfield, both of N.J.

[73] Assignee: Merck & Co., Inc., Rahway, N.J.

[21] Appl. No.: 30,510

[22] Filed: Mar. 12, 1993

Related U.S. Application Data

[60] Division of Ser. No. 938,310, Aug. 28, 1992, Pat. No. 5,223,483, which is a continuation of Ser. No. 759,128, Sep. 10, 1991, which is a continuation of Ser. No. 244,431, Sep. 16, 1988, which is a continuation-in-part of Ser. No. 112,600, Oct. 27, 1987, abandoned.

[51] Int. Cl.$^5$ .............................. C12N 15/18
[52] U.S. Cl. .................. 536/23.51; 536/23.5; 530/399
[58] Field of Search .......... 536/23.1, 23.5, 23.51; 435/69.1, 69.4, 320.1, 240.2; 530/399

[56] References Cited

U.S. PATENT DOCUMENTS

| | | |
|---|---|---|
| 4,444,760 | 4/1984 | Thomas, Jr. et al. ............ 530/399 |
| 4,518,584 | 5/1985 | Mark et al. ................... 435/69.1 |
| 4,677,064 | 6/1987 | Mark et al. ................... 435/69.1 |
| 4,752,585 | 6/1988 | Koths et al. .................. 435/256 |
| 4,835,260 | 5/1989 | Shoemaker et al. ............. 530/367 |

FOREIGN PATENT DOCUMENTS

| | | |
|---|---|---|
| 131150 | 1/1985 | European Pat. Off. |
| 142344 | 5/1985 | European Pat. Off. |
| 225701 | 1/1987 | European Pat. Off. |
| 267795 | 11/1987 | European Pat. Off. |
| 298723 | 7/1988 | European Pat. Off. |
| 87/01728 | 3/1987 | PCT Int'l Appl. |
| 87/05332 | 9/1987 | PCT Int'l Appl. |

OTHER PUBLICATIONS

Abraham et al., J. Cell Biochem. Supp. vol. 0, No. 11, Part A p. 50 (1987).
Anderson and Kingston, Proc. Natl. Acad. Sci. USA 80, pp. 6838–6842 (1983).
Armelin, Proc. Natl. Acad. Sci. USA 70, pp. 2702–2706 (1973).
Aviv and Leder, Proc. Natl. Acad. Sci USA 69, pp. 1408–1412 (1972).
Barritault et al., J. Neurosci, Res. 8, pp. 477–490 (1982).
Beaucage and Caruthers, Tetrahedron Letters 22, pp. 1859–1862 (1981).
Brosius, Gene 27, pp. 161–172 (1984).
DeBoer et al., Proc. Natl. Acad. Sci. USA 80, pp. 21–25 (1983).
esch et al., Proc. Natl. Acad. Sci. USA 82, pp. 6507–6511 (1985).
Fiddes et al., J. Cell Biochem. vol. 32, Suppl. 10C, L146, p. 149 (1986).
Fourtanier et al., J. Invest. Dermatal. 87, pp. 76–80 (1986).
Gautschi-Sova et al., Biochem. Biophys. Res. Comm. 140, pp. 874–880 (1986).
Gentz et al., Proc. Natl. Acad. Sci. USA 78, pp. 4936–4940 (1981).
Gimenez-Gallego et al., Science 230, pp. 1385–1388 (1985).
Gimenez-Gallego et al., Biochem. Biophys. Res. Commun. 138, pp. 611–617 (1986).
Gospodarowicz et al., J. Cell Biol. 97, pp. 1677–1685 (1983).
Greisler et al., Tras. am. Soc. Artif. Intern. Organs, vol. XXXII, 346–349 (1986).

(List continued on next page.)

*Primary Examiner*—Keith Baker
*Attorney, Agent, or Firm*—John W. Wallen, III; Jack L. Tribble; Paul D. Matukaitis

[57] ABSTRACT

Mutant human acidic fibroblast growth factor proteins are recombinantly produced having replaced cysteine residues with amino acids incapable of disulfide bond formation. The recombinantly produced mutant human acidic fibroblast growth factor proteins have improved biological activity in the absence of heparin when compared to wild-type recombinant human acidic fibroblast growth factor.

4 Claims, 2 Drawing Sheets

OTHER PUBLICATIONS

Harper et al., Biochem. 25, pp. 4097–4103 (1986).
Hoffman, Growth 4, pp. 361–376 (1940).
Itakura et al., Sci. 198, pp. 1056–1063 (1977).
Jay et al., Science 23, pp. 541–545.
Kuo et al., Fed. Proc. 44, p. 695 (1985).
Linemeyer et al., Bio. Tech. 5, pp. 960–965 (1987).
Maniatis et al., Cell 15, pp. 687–701.
Matteucci and Caruthers, J. Am. Chem. Soc. 103, pp. 3185–3191 (1981).
Maxam and gilbert, Proc. Natl. Acad. Sci., USA 74, pp. 560–564 (1977).
Maxam and Gilbert, Methods In Enzymology 65, pp. 499–560 (1980).
Norris et al., Nucelic Acids Res. 11, pp. 5103–5112 (1983).
O'Farrell, J. Biol. Chem. 250, pp. 4007–4021 (1975).
Sanger et al., Proc. Natl. Acad. Sci. USA 74, pp. 5463–5467 (1977).
Smithies et al., Science 202, pp. 1284–1289 (1987).
Suggs et al., Proc. Natl. Acad. Sci. USA 78, pp. 6613–6617 (1981).
Thomas et al., Proc. Natl. Acad. Sci. USA 81, pp. 357–361 (1984).
Thomas et al., Proc. Natl. Acad. Sci. USA 82, pp. 6409–6413 (1985).
Thomas and Gimenez-Gellego, TIBS 11, pp. 81–84 (1986).
Thomas et al., J. Biol. Chem. 255, pp. 5517–5520 (1980).
Trowell et al., J. Exp. Biol. 16, pp. 60–70 (1939).
Tseng et al., Eur. J. Biochem. 122, pp. 355–360 (1982).
Wensink et al., Cell 3, pp. 315–325 (1974).
Vlodavsky et al., J. Cell Biol, 83, pp. 468–486 (1979).
Zoller and Smith, Methods in Enzymology 100, pp. 468–500 (1983).
Zoller and Smith, DNA 3, pp. 479–488 (1984).
Bohlen et al., Proc. Natl. Acad. Sci. USA 81, pp. 5364–5368 (1984).
Burgess et al., Proc. Natl. Acad. Sci. USA 83, pp. 7216–7220 (1986).
Canalis et al., J. Clin. Invest. 79, pp. 52–58 (1987).
Crabb et al., biochem., 25, pp. 4988–4993 (1986).
Esch et al., Biochem. Biophys. Res. Comm. 133, pp. 554–562 (1985).
Gimenez-Gellego et al., Biochem. Biophys. Res. Comm. 135, pp. 541–548 (1986).
Gospodarowicz et al., Proc. Natl. Acad. Sci. USA 73, pp. 4120–4124 (1976).
Gospodarowicz et al., Natl. Cancer Inst. Monog. 48, pp. 109–130 (1978).
Lemmon and Bradshaw, J. Cell. Biochem. 21, pp. 195–208 (1983).
Lobb and Fett, Biochem. 23, pp. 6296–6299 (1984).
Maciag et al., Science 225, pp. 932–935 (1984).
Maniatis et al., Molecular Cloning, A Lab., Cold Spring Harbor, N.Y. pp. 217–246, 270–294, 353–361 (1982).
Schoner et al., Proc. Natl. Acad. Sci. USA 83, pp. 8506–8510 (1986).
Schreiber et al., J. Cell Biol. 101, pp. 1623–1626 (1985).
Thomas et al., J. prot. Chem. 6, pp. 163–171 (1987).
Seno, et al., Biochem. Biphys. Res. Comm. 151, pp. 701–708 (1988).
Linemeyer et al. (1990) Growth Factors 3(4), 287–293; Abstract only.
Ortega et al. (1991) J. Biol. Chem. 266(9), 5842–5846.
Seeburg et al. (1983) DNZ 2(1), 37–45.

ions Ser. No. 07/244,431 filed Sep. 16, 1988, which is a

CYSTEINE-MODIFIED ACIDIC FIBROBLAST GROWTH FACTOR

RELATED U.S. APPLICATION DATA

This is a division of application Ser. No. 07/938,310, filed Aug. 28, 1992, now U.S. Pat. No. 5,223,483, which is a continuation of application Ser. No. 07/759,128 filed Sep. 10, 1991, which is a continuation of application Ser. No. 07/244,431 filed Sep. 16, 1988, which is a continuation-in-part application of application Ser. No. 07/112,600 filed Oct. 27, 1987, now abandoned.

BACKGROUND OF THE INVENTION

Figure 1:
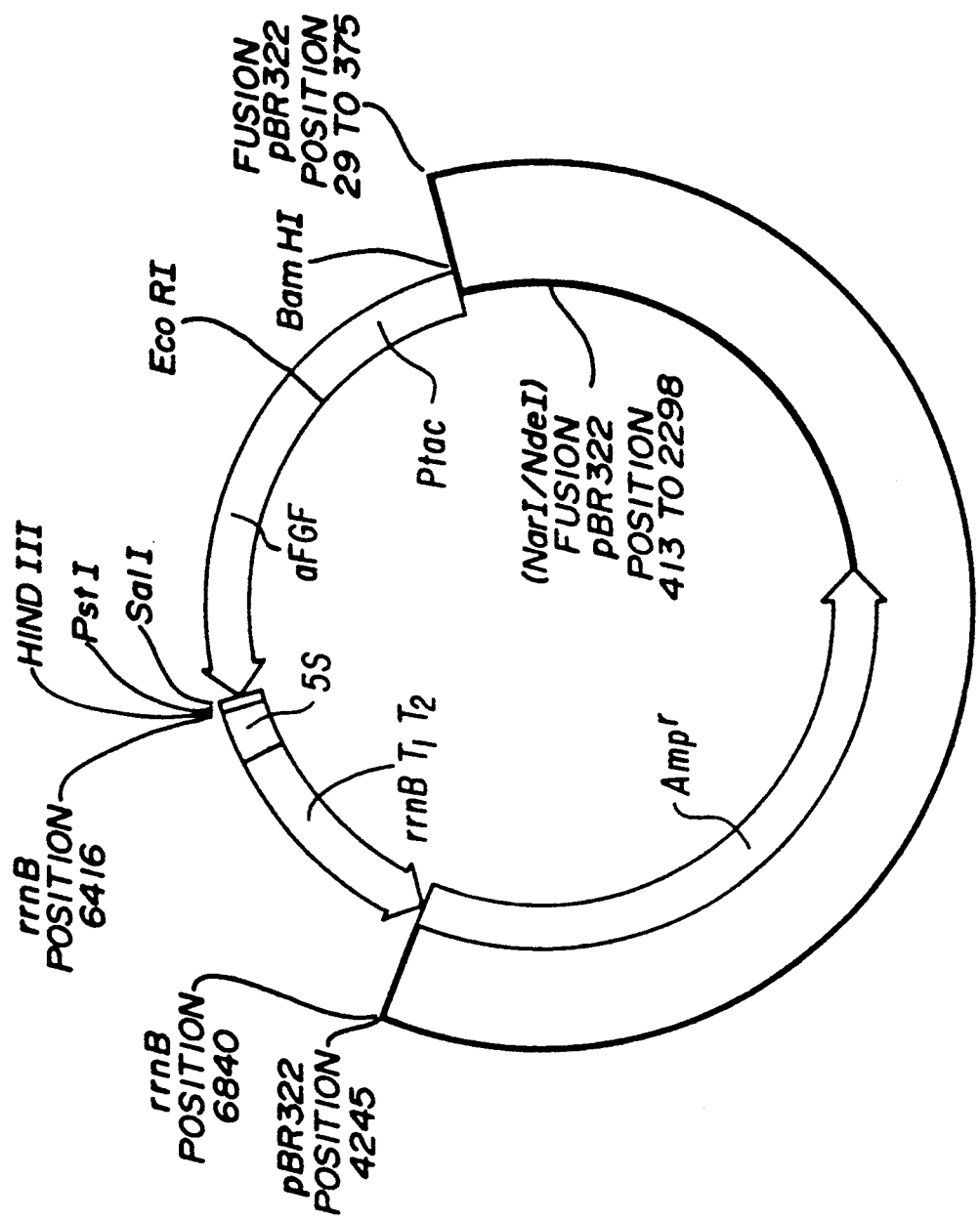
FIG. 1 is a diagram of the pKK223-3 plasmid containing a gene for mutant r-aFGF.

The discovery of substances that control the growth of animal cells, especially human cells, and the mechanism by which they work is currently one of the major focuses of biomedical research concerned with tissue repair and wound healing. Fibroblast growth factors (FGFs), mitogens for various cell types including many cells of mesodermal origin, have been identified and it has been suggested that they may induce mitosis which will result in tissue repair. Fibroblast mitogenic activity was first observed with extracts of tissue from the central nervous system. Brain-derived fibroblast mitogens were first described by Trowell et al., J,. Exp. Biol. 16: 60–70 (1939) and Hoffman, Growth 4: 361–376 (1940). It was subsequently shown that pituitary extracts also had potent mitogenic activity for fibroblastoid cells, Amelin, Proc. Natl. Acad. Sci. USA 70: 2702–2706 (1973). Partial purification of both brain and pituitary fibroblast growth factor revealed mitogenic activity for a variety-of cell types of differentiated cells including vascular endothelial cells, Gospodarowicz et al., Natl. Cancer Inst. Monogr. 48: 109–130 (1978). Fibroblast growth factor was originally thought to be a single peptide derived from the limited proteolysis of myelin basic protein. It has recently been shown that FGF exists in two forms, acidic FGF (AFGF) and basic FGF (bFGF), and both forms can be isolated and purified from mammalian brain, Thomas and Gimenez-Gallego, TIBS 11: 81–84 (1986). Numerous cell types respond to stimulation with either purified AFGF or BFGF to synthesize DNA and divide, including primary 6781P/5260A 3 176431A fibroblasts, vascular and corneal endothelial cells, chondrocytes, osteoblasts, myoblasts, smooth muscle, glial cells and neuroblasts, Esch et al., Proc. Natl. Acad. Sci. USA 82: 6507–6511 (1985); Kuo et al., Fed. Proc. 44: 695 (1985); Gensburger et al., C.R. Acad. Sc. Paris 303: 465–468 (1986). Pure bovine brain-derived AFGF not only acts as a potent mitogen for vascular endothelial cells in culture but also induces blood vessel growth in vivo, Thomas, et al. Proc. Natl. Acad. Sci. USA 82: 6409–6413 (1985). The mitogenic activity of purified AFGF can also be used to promote wound healing, Thomas, U.S. Pat. No. 4,444,760.

Acidic fibroblast growth factor was originally purified to homogeneity from bovine brain based on its mitogenic activity for BALB/C 3T3 fibroblasts, Thomas et al., Proc. Natl. Acad. Sci. USA 81: 357–361 (1984). This brain-derived growth factor has been repurified and renamed in multiple laboratories based both on its: mitogenic activity for vascular endothelial and astroglial cells (endothelial cell growth factor and astroglial growth factor 1), source (retinal-derived growth factor, eye-derived growth factor II, and perhaps brain-derived growth factor), and binding to heparin-Sepharose (class 1 heparin-binding growth factor or heparin-binding growth factor alpha), Thomas and Gimenez-Gallego TIBS 11: 81–84 (1986). The amino acid sequence of bovine AFGF has been determined, recognized to be highly homologous to basic FGF and related to the fibroblast mitogens interleukin 1-alpha and 1-beta, Gimenez-Gallego et al., Science 230: 1385–1388 (1985). The complete amino acid sequence of 6781P/5260A 4 176431A human AFGF has been determined from the purified protein, Gimenez-Gallego et al., Biochem. Biophy. Res. Comm. 138: 611–617 (1986), and from the gene, Jaye et al., Science 233: 541–545 (1986).

Native AFGF purified from brain or recombinant-derived AFGF (r-aFGF) requires the co-administration of heparin to optimally stimulate Balb/c 3T3 fibroblasts and vascular endothelial cells in culture. Human brain-derived and recombinant AFGF are only about 1% to 5% as active on these cells in culture in the absence of heparin compared to optimal activity in the presence of heparin. While the doses required for maximal AFGF activity are relatively low, it might be desirable to administer AFGF with no heparin since heparin could conceivably elicit detrimental side effects. Pure human AFGF, in addition to the standard conditions that destroy the activity of most proteins, extremes of heat, pH and the presence of proteases, is also labile to lyophilization and oxidation. The pure AFGF becomes cross-linked through intrachain or interchain disulfide bonds by oxidation and can be recovered in active form by disulfide reduction with 20 Mm dithiothreitol. Heparin can inhibit intermolecular disulfide bond mediated aggregation of AFGF. This heterogeneous glycosaminoglycan has also been noted to stabilize AFGF from heat denaturation and proteolytic degradation by trypsin. Consequently, either exogenous or endogenous heparin is required for the in vivo activity associated with tissue repair. The present invention provides unique mutated forms of recombinant-derived AFGF which have an increased biological activity in the absence of heparin compared to native AFGF.

OBJECT OF THE INVENTION

It is, accordingly, an object of the present invention to convert by mutation recombinant bovine and human AFGF genes to genes capable of encoding proteins which are more active in the absence of heparin than the native or recombinant protein. Another object is to incorporate the specific genes into appropriate cloning vectors. A further object is to transform an appropriate host with each of the recombinant vectors and to induce expression of the specific mutated AFGF genes. Another object is to isolate and purify biologically active bovine and human mutated AFGF. These and other objects of the present invention will be apparent from the following description.

SUMMARY OF THE INVENTION

Novel genes coding for mutated bovine and human AFGF are constructed. The unique genes are derived from genes encoding recombinant native bovine and human AFGF by specific point mutation. Each gene construct is inserted into an expression vector which is used to transform an appropriate host. The transformed host cells produce unique mutated recombinant AFGF, human or bovine, which is purified and has enhanced or improved biological activity in the absence of heparin compared to the uranutated forms.

DETAILED DESCRIPTION

Acidic fibroblast growth factor exists in various microheterogeneous forms which are isolated from the various tissue sources and cell types known to contain AFGF. Microheterogeneous forms as used herein refer to a single gene product, that is a protein produced from a single gene unit of DNA, which is structurally modified following translation. These structural modifications, however, do not result in any significant alterations of biological activity of the peptide. Biological activity and biologically active are used interchangably and are herein defined as the ability of native, recombinant or mutant recombinant AFGF to stimulate DNA synthesis in quiescent Balb/c 3T3 fibroblasts as described in Example 7, to stimulate any of the cell types described above or to carry out any of the functions described in the art. The modifications may take place either in vivo or during the isolation and purification process. In vivo modification results in, but is not limited to, acetylation at the N-terminus, proteolysis, glycosylation or phosphorylation. Proteolysis may include exoproteolysis wherein one or more terminal amino acids are sequentially, enzymatically cleaved to produce microheterogeneous forms which have fewer amino acids than the original gene product. Proteolysis may also include endoproteolytic modification that results from the action of endoproteases which cleave the peptide at specific locations within the amino acid sequence. Similar modifications can occur during the purification process which also results in the production of microheterogeneous forms. The most common modification occuring during purification is proteolysis which is generally held to a minimum by the use of protease inhibitors. Under most conditions a mixture of microheterogeneous forms are present following purification of native AFGF. Native AFGF refers to AFGF isolated and purified from tissues or cells that contain AFGF.

The invention is contemplated to include all animal microheterogeneous forms of acidic fibroblast growth factor. The preferred embodiments include bovine and human microheterogeneous forms of AFGF. he most preferred microheterogeneous forms of bovine aFGF include a 154 amino acid form, a 140 amino acid form and a 134 amino acid form. The 140 amino acid form is shown in Table I, Gimenez-Gallego et al., Science 230: 1385-1388 (1985), and is the most preferred of the bovine species.

TABLE I

| Amino Acid Sequence of Bovine aFGF |
|---|
| 1  10  20 |
| PheAsnLeuProLeuGlyAsnTyrLysLysProLysLeuLeuTyrCysSerAsnGlyGlyTyrPheLeuArgIleLeu |
| 30  40  50 |
| ProAspGlyThrValAspGlyThrLysAspArgSerAspGlnHisIleGlnLeuGlnLeuCysAlaGluSerIleGlyGlu |
| 60  70  80 |
| ValTyrIleLysSerThrGluThrGlyGlnPheLeuAlaMetAspThrAspGlyLeuLeuTyrGlySerGlnThrProAsn |
| 90  100 |
| GluGluCysLeuPheLeuGluArgLeuGluGluAsnHisTyrAsnThrTyrIleSerLysLysHisAlaGluLysHisTrp |
| 110  120 |
| PheValGlyLeuLysLysAsnGlyArgSerLysLeuGlyProArgThrHisPheGlyGlnLysAlaIleLeuPheLeuPro |
| 140 |
| LeuProValSerSerAsp |

The nucleotide sequence of the 140 amino acid form, recombinant, of bovine aFGF is shown in Table II.

TABLE II
Nucleotide Sequence of Bovine aFGF

```
1              20              40              60              80
AATTCATGTTCAATCTGCCACTGGGTAATTACAAAAGCCAAAGCTTCTTTACTGCTCTAACGGTGGTTACTTTCTCCGC
GTACAAGTTAGACGGTGACCCATTAATGTTTTCGGTTTCGAAGAAATGACGAGATTGCCACCAATGAAAGAGGCG 100             120             140             160
ATCCTGCCAGATGGTACCGTGGACGGCACCAAAGATCGTTCTGATCAACATATTCAACTGCAGCTGTGCGCCGAATCTAT
TAGGACGGTCTACCATGGCACCTGCCGTGGTTTCTAGCAAGACTAGTTGTATAAGTTGACGTCGACACGCGGCTTAGATA 180             200             220             240
CGGTGAAGTTTACATCAAATCTACCGAAACTGGTCAATTCCTTGCCATGGACACTGATGGCCTGCTGTACGGATCCCAGA
GCCACTTCAAATGTAGTTTAGATGGCTTTGACCAGTTAAGGAACGGTACCTGTGACTACCGGACGACATGCCTAGGGTCT 260             280             300             320
CCCCAAACGAGGAGTGCCTTTTCCTGGAGCGCCTGGAGGAAAACCATTACAACACCTACATCTCTAAAAAGCATGCTGAG
GGGGTTTGCTCCTCACGGAAAAGGACCTCGCGGACCTCCTTTGGTAATGTTGTGGATGTAGAGATTTTTCGTACGACTC 340             360             380             400
AAACATTGGTTCGTAGGCCTTAAGAAAAATGGCCGCTCTAAACTGGGCCCTCGTACTTTGGTCAAAAAGCTATCCT
TTTGTAACCAAGCATCCGGAATTCTTTTTACCGGCGAGATTTGACCCGGAGCATGAGTGAAACCAGTTTTTCGATAGGA 420             440
GTTCCTGCCACTGCCAGTCACTGCCAGTCACTGCCAGTCACTGAGCTCTGACTAATAGATATCG
CAAGGACGGTGACGGTCACTGAGCTCGAGACTGATTATCTATAGCAGCT
```

The 154 amino acid form includes the following additional amino acids; Ala-Glu-Gly-Glu-Thr-Thr-Thr-Phe-Thr-Ala-Leu-Thr-Glu-Lys, with the carboxyl terminus Lys attached to the amino terminus Phe at the first position of the 140 amino acid form. The amino terminal alanine residue of the 154 amino acid form of the bovine AFGF may be acetylated. The 134 amino acid form is identical to the 140 amino acid form except that the first 6 amino acids of the amino terminus have been removed. When native AFGF is isolated the relative amounts of these microheterogeneous forms vary depending on the process used but generally contain at least two of these forms.

Human AFGF exhibits a similar microheterogeneity to that of bovine AFGF. The most preferred microheterogeneous forms of human AFGF include a 154 amino acid form, a 140 amino acid form and a 139 amino. acid form. The human 140 amino acid form differs from the bovine form by eleven amino acids, as shown in TABLE VIII. The 154 amino acid form contains the exact sequence of the human 140 amino acid form plus the 14 additional amino acids associated with the bovine 154 amino acid form, with one exception.

The amino acid at the fifth position of the N-terminus or at the -10 position as determined from the 140 amino acid Phe N-terminus in the human form is isoleucine and is substituted for the threonine in the bovine form. The additional 14 amino acid human N-terminal sequence is; Ala-Glu-Gly-Glu-Ile-Thr-Thr-Phe-Thr-Ala-Leu-Thr-Glu-Lys. The additional amino acids of the 154 amino acid form are numbered from the N-terminal Ala, -14, to the carboxyl terminal Lys,-1. The amino terminal alanine resiude at the -14 position may be acetylated. A third form of human aFGF contains 139 amino acids and is equivalent to the human 140 amino acid form with the amino terminal phenylalanine residue removed. The amino terminal asparagine residue may be deamidated to aspartic acid in the 139 amino acid form of human aFGF. The 140 and 139 amino acid forms are the most preferred forms of the human microheterogeneous forms. The 140 amino acid form is shown in Table III, Gimenez-Gallego et al., Biochem. Biophys. Res. Comm. 138: 611–617 (1986)

TABLE III

| Amino Acid Sequence of Human aFGF |
|---|
| 1　　　　　　　　　　　　　　　　10　　　　　　　　　　　　　　　　20<br>PheAsnLeuProProGlyAsnTyrLysLysProLysLeuLeuTyrCysSerAsnGlyGlyHisPheLeuArgIleLeu |
| 30　　　　　　　　　　　　　　　　40　　　　　　　　　　　　　　　　50<br>ProAspGlyThrValAspGlyThrArgAspArgSerAspGlnHisIleGlnLeuGlnLeuSerAlaGluSerValGlyGlu |
| 60　　　　　　　　　　　　　　　　70　　　　　　　　　　　　　　　　80<br>ValTyrIleLysSerThrGluThrGlyGlnTyrLeuAlaMetAspThrAspGlyLeuLeuTyrGlySerGlnThrProAsn |
| 90　　　　　　　　　　　　　　　　100<br>GluGluCysLeuPheLeuGluArgLeuGluGluAsnHisTyrAsnThrTyrIleSerLysLysHisAlaGluLysAsnTrp |
| 110　　　　　　　　　　　　　　　120　　　　　　　　　　　　　　　130<br>PheValGlyLeuLysLysAsnGlySerCysLysArgGlyProArgThrHisTyrGlyGlnLysAlaIleLeuPheLeuPro |
| 140<br>LeuProValSerSerAsp |

The nucleotide sequence of the 140 amino acid form, recombinant, of human aFGF is shown in Table IV.

TABLE IV

Nucleotide Sequence of Human aFGF

```
1                    20                    40                    60                    80
AATTCATGTTCAATCTGCCACCGGGTAATTACAAAAAGCCAAAGCTTCTTTACTGCTCTAACGGTGGTCACTTTCTCCGC
GTACAAGTTAGACGGTGGCCCATTAATGTTTTCGGTTTCGAAGAAATGACGAGATTGCCACCAGTGAAAGAGGCG 100                   120                   140                   160
ATCCTGCCAGATGGTACCGTGGACGGCACCAGAGATCGTTCTGATCAACATATTCAACTGCAGCTGTCCGCCGAATCTGT
TAGGACGGTCTACCATGGCACCTGCCGTGGTCTCTAGCAAGACTAGTTGTATAAGTTGACGTCGACAGGCGGCTTAGACA 180                   200                   220                   240
CGGTGAAGTTTACATCAAATCTACCGAAACTGGTCAATACCTTGCCATGGACACTGATGGCCTGCTGTACGGATCCCAGA
GCCACTTCAAATGTAGTTTAGATGGCTTTGACCAGTTATGGAACGGTACCTGTGACTACCGGACGACATGCCTAGGGTCT 260                   280                   300                   320
CCCCAAACGAGGAGTGCCTTTTCCTGGAGCGCCTGGAGGAAAACCATTACAACACCTACATCTCTAAAAAGCATGCTGAG
GGGGTTTGCTCCTCACGGAAAAGGACCTCGCGGACCTCGCGGACCTCCTTTTGGTAATGTTGTGGATGTAGAGATTTTTCGTACGACTC 340                   360                   380                   400
AAAAATTGGTTCGTAGGCCTTAAGAAAAATGGCAGCTGTAAACGCGGGCCCTCGTACTCACTATGGCCAAAAAGCTATCCT
TTTTTAACCAAGCATCCGGAATTCTTTTTACCGTCGACATTTGCGCCCGGGAGCATGAGTGATACCGGTTTTTCGATAGGA 420                   440
GTTCCTGCCACTGCCAGTGAGCTCTGACTAATAGATATCG
CAAGGACGGTGACGGTCACTCGAGACTGATTATCTATAGCAGCT
```

The preferred procedure for obtaining a gene for mammalian aFGF is to synthesize the gene because this allows optimization of translated protein and ease of mutagenesis. The gene may be synthesized based on the amino acid sequence of a microheterogeneous form of aFGF obtained from any animal including man. The preferred method is to use the bovine amino acid sequence for AFGF and chemically point mutate the base sequence, to produce the genes for other species, Linemeyer et al. Biotechnol. 5:960-965 (1987).

The synthetic genes are based on the determined bovine amino acid sequence described by Gimenez-Gallego et al., Science 230: 1385-1388 (1985) and the human amino acid sequence as described by Gimenez-Gallego et al. Biochem. Biophys. Res. Comm., 138: 611-617 (1986) and shown in Tables I and III. The unique nucleotide sequence of the 140 amino acid form of bovine AFGF is derived from reverse translation of the amino acid sequence by a technique similar to that of Itakura et al., Science 198: 1056-1063 (1977). The various novel nucleotide sequences corresponding to the native amino acid sequence of bovine AFGF are shown in the following table:

TABLE V

```
                    5                        10                       15                       20
     Phe  Asn  Leu  Pro  Leu  Gly  Asn  Tyr  Lys  Lys  Pro  Lys  Leu  Leu  Tyr  Cys  Ser  Asn  Gly  Gly
     TTQ  AAQ  CTN  CCN  CTN  GGN  AAQ  TAQ  AAP  AAP  CCN  AAP  CTN  CTN  TAQ  TGQ  TCN  AAQ  GGN  GGN
               TTP       TTP                                      TTP  TTP            AGQ 25                       30                       35                       40
     Tyr  Phe  Leu  Arg  Ile  Leu  Pro  Asp  Gly  Thr  Val  Asp  Gly  Thr  Lys  Asp  Arg  Ser  Asp  Gln
     TAQ  TTQ  CTN  CGN  ATQ  CTN  CCN  GAQ  GGN  ACN  GTN  GAQ  GGN  ACN  AAP  GAQ  CGN  TCN  GAQ  CAP
               TTP  AGP  ATA  TTP                                                                 AGP  AGQ 45                       50                       55                       60
     His  Ile  Gln  Leu  Gln  Leu  Cys  Ala  Glu  Ser  Ile  Gly  Glu  Val  Tyr  Ile  Lys  Ser  Thr  Glu
     CAQ  ATQ  CAP  CTN  CAP  CTN  TGQ  GCN  GAP  TCN  ATQ  GGN  GAP  GTN  TAQ  ATQ  AAP  TCN  ACN  GAP
          ATA       TTP       TTP                 AGQ  ATA                      ATA            AGQ 65                       70                       75                       80
     Thr  Gly  Gln  Phe  Leu  Ala  Met  Asp  Thr  Asp  Gly  Leu  Leu  Tyr  Gly  Ser  Gln  Thr  Pro  Asn
     ACN  GGN  CAP  TTQ  CTN  GCN  ATG  GAQ  ACN  GAQ  GGN  CTN  CTN  TAQ  GGN  TCN  CAP  ACN  CCN  AAQ
                         TTP                                           TTP  TTP            AGQ 85                       90                       95                       100
     Glu  Glu  Cys  Leu  Phe  Leu  Glu  Arg  Leu  Glu  Glu  Asn  His  Tyr  Asn  Thr  Tyr  Ile  Ser  Lys
     GAP  GAP  TGQ  CTN  TTQ  CTN  GAP  CGN  CTN  GAP  GAP  AAQ  CAQ  TAQ  AAQ  ACN  TAQ  ATQ  TCN  AAP
                    TTP       TTP            AGP  TTP                                                ATA  AGQ 105                      110                      115                      120
     Lys  His  Ala  Glu  Lys  His  Trp  Phe  Val  Gly  Leu  Lys  Lys  Asn  Gly  Arg  Ser  Lys  Leu  Gly
     AAP  CAQ  GCN  GAP  AAP  CAQ  TGG  TTQ  GTN  GGN  CTN  AAP  AAP  AAQ  GGN  CGN  TCN  AAP  CTN  GGN
                                             TTP                                     AGP  AGQ       TTP 125                      130                      135                      140
     Pro  Arg  Thr  His  Phe  Gly  Gln  Lys  Ala  Ile  Leu  Phe  Leu  Pro  Leu  Pro  Val  Ser  Ser  Asp
     CCN  CGN  ACN  CAQ  TTQ  GGN  CAP  AAP  GCN  ATQ  CTN  TTQ  CTN  CCN  CTN  CCN  GTN  TCN  TCN  GAQ
     AGP                                          ATA  TTP       TTP       TTP                 AGQ  AGQ
```

Where Q = C or T, P = A or G, and N = A, T, C, or G

The bovine gene is constructed with a leader portion containing a single restriction enzyme cleavage site and an N-terminal methionine codon for a translational start site. The gene also contains a tail containing tandem translational stop codons and two restriction enzyme cleavage sites. The redundancy of the genetic code allows a choice of base sequences which in turn allows for the incorporation of unique restriction enzyme cleavage sites throughout the gene. The preferred bovine gene base sequence with the location of the restriction enzyme cleavage sites is shown in the following table:

TABLE VI

```
          1                                        10
     Met  Phe  Asn  Leu  Pro  Leu  Gly  Asn  Tyr  Lys  Lys  Pro  Lys  Leu  Leu    Tyr  Cys  Ser    Asn  Gly

[1]
            20                       40                        .                60
     AATTCATGTTCAATCTGCCACTGGGTAATTACAAAAAGCCAAAGCTTCT  TTACTGCTC  TAACGGT
     GTACAAGTTAGACGGTGACCCATTAATGTTTTTCGGTTTCGAAGA      AATGACGAG  ATTGCCA
                          [2]
     (EcoRI)                                           HindIII 20                          30
          Gly  Tyr  Phe  Leu  Arg  Ile  Leu  Pro  Asp  Gly  Thr  Val  Asp  Gly  Thr  Lys  Asp  Arg  Ser

[3]
                  80                        100                         .         120
     GGTTACTTTCTCCGCATCCTGCCAGATGGTACCGTGGACGGCA CCAAAGATCG TTCT
     CCAATGAAAGAGGCGTAGGACGGTCTACCATGGCACCTGCCGT GGTTTCTAGC AAGA
                                       [4]
                                                     KpnI
```

TABLE VI-continued

```
                40                              50
Asp Gln His Ile Gln Leu Gln Leu Cys Ala Glu Ser Ile Gly Glu Val Tyr Ile Lys Ser Thr
                           [5]
                 140                   160                180
        GATCAACATATTCAACTGCAGCTGTGCGCCGAATCTATCGGT|GAAGTTTAC ATCAAATCTACC
        CTAGTTGTATAAGTTGACGTCGACACGCGGCTTAGATAGCCA CTTCAAATG|TAGTTTAGATGG
                                     [6]
BclI           PstIPvuII              HinfI 60                                70
         Glu Thr Gly Gln Phe Leu Ala Met Asp Thr Asp Gly Leu Leu Tyr Gly  Ser  Gln Thr
                    [7]
                      200                   220                       240
         GAAACTGGTCAATTCCTTGCCATGGACACTGATGGCCTGCTGTACG|GATC CCAGACC
         CTTTGACCAGTTAAGGAACGGTACCTGTGACTACCGGACGACATGC CTAG|GGTCTGG
                                 [8]
                         NcoI                                  BamHI 80                                   90
Pro Asn Glu Glu Cys Leu Phe Leu Glu Arg Leu Glu Glu Asn His Tyr Asn Thr Tyr Ile
              [9]
               260                   280                   300
CCAAACGAGGAGTGCCTTTTCCTGGAGCGCCTGGAGGAAAA|CCATTACAAC ACCTACATC
GGTTTGCTCCTCACGGAAAAGGACCTCGCGGACCTCCTTTT GGTAATGTTG|TGGATGTAG
                       [10]
                                                HaeII 100                                110
    Ser Lys Lys His Ala Glu Lys His Trp Phe Val Gly Leu Lys Lys Asn Gly Arg Ser Lys
              [11]
                  320                          340                   360
        TCTAAAAAGCATGCTGAGAAACATTGGTT|CGTAGGCC TTAAGAAAAATGGCCGCTCTAAA
        AGATTTTTCGTACGACTCTTTGTAACCAA GCATCCGG|AATTCTTTTACCGGCGAGATTT
                          [12]
                      SphI                         StuI 120                                   130                            140
Leu Gly Pro Arg Thr His Phe Gly Gln Lys Ala Ile Leu Phe Leu Pro Leu Pro Val Ser Ser Asp   .   .
     [13]                                                                  [15]
           380                   400                         420
CTGGGCCCTCGTACTCACTTTG|GTCAAAAAGC TATCCTGTTCCTGCCACTGCCAGTGAGCTCTGACTAATA
GACCCGGGAGCATGAGTGAAAC CAGTTTTTCG|ATAGGACAAGGACGGTGACGGTCACTCGAGACTGATTAT
                 [14]                                                        [16]
        ApaI                                                         SacI 440
                                                                   GATATCG      440
                                                                   CTATAGCAGCT EcoRV  (SalI)
```

The gene sequence for each strand of the double-stranded molecule is randomly divided into 8 nucleotide sequences. The oligonucleotides are constructed with overlapping ends to allow the formation of the double-stranded DNA. The following table contains one of a multitude of oligonucleotide arrangements that is used to produce the bovine AFGF gene.

TABLE VII

```
OLIGO-1       10         20         30         40         50       58
5'    AATTCATGTT CAATCTGCCA CTGGGTAATT ACAAAAAGCC AAAGCTTCTT TACTGCTC 3'

OLIGO-2       10         20         30         40     45
5'    AGAAGCTTTG GCTTTTTGTA ATTACCCAGT GGCAGATTGA ACATG 3'

OLIGO-3       10         20         30         40         50        60
5'    TAACGGTGGT TACTTTCTCC GCATCCTGCC AGATGGTACC GTGGACGGCA CCAAAGATCG 3'

OLIGO-4       10         20         30         40         50       59
5'    TGCCGTCCAC GGTACCATCT GGCAGGATGC GGAGAAAGTA ACCACCGTTA GAGCAGTAA 3'

OLIGO-5       10         20         30         40     46
5'    TTCTGATCAA CATATTCAAC TGCAGCTGTG CGCCGAATCT ATCGGT 3'

OLIGO-6       10         20         30         40         50     60   65
5'    GTAAACTTCA CCGATAGATT CGGCGCACAG CTGCAGTTGA ATATGTTGAT CAGAACGATC TTTGG 3'
```

TABLE VII-continued

```
OLIGO-7        10         20         30         40         50         60      67
5'    GAAGTTTACA TCAAATCTAC CGAAACTGGT CAATTCCTTG CCATGGACAC TGATGGCCTG CTGTACG 3'

OLIGO-8        10         20         30         40         50       60   62
5'    GATCCGTACA GCAGGCCATC AGTGTCCATG GCAAGGAATT GACCAGTTTC GGTAGATTTG AT 3'

OLIGO-9        10         20         30         40         50  52
5'    GATCCCAGAC CCCAAACGAG GAGTGCCTTT TCCTGGAGCG CCTGGAGGAA AA 3'

OLIGO-10       10         20         30         40         50         58
5'    GTTGTAATGG TTTTCCTCCA GGCGCTCCAG GAAAAGGCAC TCCTCGTTTG GGGTCTGG 3'

OLIGO-11       10         20         30         40      48
5'    CCATTACAAC ACCTACATCT CTAAAAAGCA TGCTGAGAAA CATTGGTT 3'

OLIGO-12       10         20         30         40      46
5'    GGCCTACGAA CCAATGTTTC TCAGCATGCT TTTTAGAGAT GTAGGT 3'

OLIGO-13       10         20         30         40         50  53
5'    CGTAGGCCTT AAGAAAAATG GCCGCTCTAA ACTGGGCCCT CGTACTCACT TTG 3'

OLIGO-14       10         20         39         40         50   55
5'    GCTTTTTGAC CAAAGTGAGT ACGAGGGCCC AGTTTAGAGC GGCCATTTTT CTTAA 3'

OLIGO-15       10         20         30         40         50    56
5'    GTCAAAAAGC TATCCTGTTC CTGCCACTGC CAGTGAGCTC TGACTAATAG ATATCG 3'

OLIGO-16       10         20         30         40         50
5'    TCGACGATAT CTATTAGTCA GAGCTCACTG GCAGTGGCAG GAACAGGATA 3'
```

The oligonucleotides illustrated in Table VII are presented merely as an example of oligonucleotide subunits and should not be construed as limiting thereto. The composite base sequence showing the overlap and arrangement of the oligonucleotides is illustrated in Table II.

The bovine gene is assembled in 2 steps: first, the half corresponding to the N-terminal portion of the protein; and second, the C-terminal half. Generally, the oligonucleotides are kinased with T4 polynucleotide kinase in the presence of either ATP or $^{32}$P-labelled ATP. In the first reaction of each step the oligonucleotides which make up one strand of the gene are kinased with the exception of the most 5' oligonucleotide. In the second reaction the oligonucleotides which make up the second strand are kinased, with the exception of the most 5' oligonucleotide. When kinased oligonucleotides are used, about 1% of the added oligonucleotide is $^{32}$P-labelled for later identification of the products. Annealing is carried out in an appropriate buffer, such as one containing but not limited to about 60 mM TRIS, about pH 7.6, about 5 mM dithiothreitol (DTT), about 10 mM MgCl$_2$ and about 30 μM ATP at about 90° C. for about 4 minutes followed by a rapid transfer to about 60° C. and a slow cooling to about 30° C. Ligation is carried out in an appropriate buffer, such as one containing, but not limited to, about 60 mM TRIS, about pH 7.6, about 10 mM DTT, about 10 Mm MgCl$_2$, about 1 mM ATP, and about 0.03 units T4 DNA ligase at about 20° C. for about 1 and ½ hour.

The ligated oligonucleotides are purified by polyacrylamide gel electrophoresis following ethanol precipitation. The oligonucleotides are redissolved in a buffer containing about 20 μl of about 80% formamide, about 50 mM TRIS-borate, about pH 8.3, about 1 mM ethylenediaminetetraacetic acid (EDTA), about 0.1% (w/v) xylene cyanol, and about 0.1% (w/v) bromophenol blue. Each sample is heated at about 90° C. for about 3 minutes and electrophoresed in about a 10% urea-polyacrylamide gel at about 75 watts for about 5 hours. The 231 base N-terminal bands are removed, combined and eluted at about 4° C. in about 0.5 M ammonium acetate containing about 1 mM EDTA at about pH 8. The 209 base C-terminal bands are treated in the same manner.

The synthetic gene sequences coding for either the N-terminal or the C-terminal portions of the AFGF are incorporated into the pBR322 plasmid. It is especially desired and intended that there be included within the scope of this invention, the use of other plasmids into which the AFGF gene can be incorporated and which will allow the expression of the AFGF gene. Reannealed oligonucleotides, about 300 fmole and about 100 fmole of the recovered 231 base pair N-terminus are each ligated to about 100 fmole of agarose gel-purified about 3.9 kilo base (kb) EcoRI-BamHI pBR322 for the N-terminus. The 209 bp C-terminus is constructed in the same manner using BamHI-SalI pBR322. Ligation is carried out in a buffer containing about 25 Mm TRIS, about pH 7.6, about 1 mM DTT, about 10 Mm MgCl about 0.4 mM ATP, with about 1 unit of T4 DNA ligase for about 1 hour at about 20° C. Each half-gene ligated vector is used to transform competent bacterial cells, such as E. coli RR1 (Bethesda Research Laboratories, BRL) following suppliers procedures. The transformed cells are selected for growth in ampicillin and screened for the presence of either the 231 base pair (bp) EcoRI-BamHI insert or the 209 bp BamHI-SilI insert by restriction analysis of mini-lysate plasmid preparations.

The DNA sequence of clones containing the appropriate sized inserts is determined using Maxam and Gilbert, Proc. Natl. Acad. Sci. USA 74: 560–564 (1977) chemical DNA sequence techniques.

The final full-length AFGF synthetic gene was cloned by cleaving the N-terminal half clone with restriction enzymes BamHI and SalI, treating with alkaline phosphatase and ligating this to the gel purified 209 bp BamHI-SalI insert of the C-terminal half clone. This ligated material was used to transform competent RR1 cells as before.

Expression of the synthetic AFGF gene is accomplished by a number of different promoter-expression systems. It is desired and intended that there be included within the scope of this invention, the use of other promoter-expression systems for the expression of the intact AFGF gene. The preferred construct uses the E. coli tac promoter, a hybrid between regions of the trp promoter and the lac promoter as described by deboer et al., Proc. Nat. Acad. Sci. USA 80: 21-25 (1983). Plasmid pKK223-3 (Pharmacia) which contains the tac promoter and rrnb rRNA transcription terminator was modified to remove the pBR322-derived SalI restriction enzyme site. The rrnB RRNA terminator has been shown to allow expression by strong promoters, Gentz et al., Proc. Natl. Acad. Sci. USA 78: 4936-4940 (1981); Brosius, Gene 27: 161-172 (1984).

The pKK223-3 plasmid DNA is cleaved with restriction enzymes to produce a 2.7 kb DNA fragment to generate clone pKK2.7. The synthetic AFGF gene is cleaved from its pBR322 vector and transferred to the pKK2.7 plasmid after restricting pKK2.7 with EcoRI and SalI. The resulting recombinant, shown in figure 1, is transformed into E. coli JM105 (Pharmacia) or DH5 (BRL) cells and expressed.

Site specific mutagenesis is an efficient Way to convert the amino acid sequence of one mammalian species of AFGF to the AFGF amino acid sequence of another species. The following description relates to the site specific mutagenic conversion of bovine AFGF, 140 amino acid form (numbered in accordance with the native form), to human AFGF, it is to be understood, however, that the process can be used to convert any mammalian species aFGF to that of any other species. The only limitation on the conversion is that the amino acid sequences of both aFGFs must be known. The following table lists the amino acids which must be substituted and the location on the bovine AFGF amino acid map, Table VI, at which the substitutions are made:

TABLE VIII

| Amino Acid | Substituted Amino Acids | |
|---|---|---|
| Location | Human aFGF | for Bovine aFGF |
| 5 | Pro | Leu |
| 21 | His | Tyr |
| 35 | Arg | Lys |
| 47 | Ser | Cys |
| 51 | Val | Ile |
| 64 | Tyr | Phe |
| 106 | Asn | His |
| 116 | Ser | Arg |
| 117 | Cys | Ser |
| 119 | Arg | Leu |
| 125 | Tyr | Phe |

As with the bovine gene sequence eight oligonucleotides representing the human gene sequence are constructed by the same procedure as that used for the bovine oligonucleotides. The following table contains one of a multitude of oligonucleotide arrangements that is used to produce the human aFGF gene.

TABLE IX

OLIGO-1
5'   CTGCCACCGGGTAATTAC 3'

OLIGO-2
5'   CGGTGGTCACTTTCTCCG 3'

OLIGO-3
5'   CGGCACCAGAGATCGTTC 3'

TABLE IX-continued

OLIGO-4
5'   GCAGCTGTCCGCCGAATCTGTCGGTGAAG 3'

OLIGO-5
5'   CTGGTCAATACCTTGCCATGG 3'

OLIGO-6
5'   GCTGAGAAAAATTGGTTCG 3'

OLIGO-7
5'   GGCCGCGTTTACAGCTGCCATTTTTCTTAAGG 3'

OLIGO-8
5'   CGTACTCACTATGGCCAAAAAGCTATCC 3'

The cloned synthetic bovine gene for AFGF is converted to a human synthetic gene for AFGF by a series of directed point mutations. Oligonucleotide-directed mutagenesis of the cloned gene allows the alteration of the base sequence of bovine AFGF so that the resulting amino acid sequence contains the substituted amino acids shown in Table VIII and is human AFGF. A deletion is made in the bovine gene to remove the amino terminal phenylalanine for the production of the human 139 amino acid microheterogeneous form of AFGF. A point mutation is carried out to replace the second position asparagine with aspartic acid. Alternatively, the asparagine is deamidated to aspartic acid. The methods for carrying out these procedures are described below or are known in the art. The oligonucleotide-directed mutagenesis is carried out using standard procedures known to the art, Zoller and Smith, Methods in Enzymology, 100: 468-500 (1983); Norris et al., Nucleic Acids Research, 11: 5103-5112 (1983); and Zoller and Smith, DNA, 3: 479-488 (1984). The point mutations of the bovine to human conversion are carried out by the standardized oligonucleotide-directed mutagenesis and are shown in the following Table. The location of the base mutagenesis can be seen in Table X.

TABLE X

| | Substituted Base | | |
|---|---|---|---|
| Base Location | Human aFGF | for Bovine aFGF | Corresponding Human Amino Acid |
| 22 | C | T | Pro |
| 69 | C | T | His |
| 112 | G | A | Arg |
| 148 | C | G | Ser |
| 159 | G | A | Val |
| 199 | A | T | Tyr |
| 324 | A | C | Asn |
| 354 | A | C | Ser |
| 358 | G | C | Cys |
| 364 | G | T | Arg |
| 365 | C | G | Arg |
| 382 | A | T | Tyr |

To expedite the mutagenesis of the bovine AFGF gene it is transferred to a standard vector, M13mp19, a single-stranded DNA bacteriophage vector. The bovine pKK-aFGF plasmid is cleaved with EcoRI and SalI and the resulting 440 bp fragment is gel purified. Vector M13mp19 RF DNA is cleaved with the same two endonucleases and the ends are subsequently dephosphorylated with bacterial alkaline phosphatase. The vector DNA and the AFGF gene fragment DNA are ligated and the mixture is used to transform E. coli DH5 cells. A phage clone containing the bovine AFGF gene is selected, M13MP19-baFGF.

The human oligomers shown in Table IX are phosphorylated and annealed individually to M13mp19-baFGF single-stranded phage DNA.. Closed-circular double-stranded molecules are prepared with T4 DNA ligase and DNA polymerase I klenow fragment. The preparations were each used to transform competent JM105 cells and the resulting transformant plaques are selected by hybridization with the appropriate oligomer which is labeled using polynucleotide kinase. Single-stranded DNA is isolated from the phage clone containing the human oligmer 4 mutations and the above procedure is repeated using the human oligomer 5 to generate a clone containing both the oligomer 4 and 5 mutations.

In the following procedures the bovine-to-human sequence mutations in these M13-based clones were combined into one pBR322-based clone. RF DNAs were prepared from clones containing the base changes specified by human oligomers 1, 2, 6, and 8. The DNA of the human 1 mutant clone was cleaved with EcoRI, the ends were dephosphorylated with bacterial alkaline phosphatase, and the DNA was cleaved with HindIII. The human 2 mutant DNA was cleaved with HindIII, treated with phosphatase, and then cleaved with BamHI. The human 6 mutant DNA was cleaved with BamHI, phosphatase treated, and subsequently cleaved with ApaI. Likewise, the human 8 mutant DNA was cleaved with ApaI, the ends were dephosphorylated, and the DNA was cleaved with SalI. These four DNA preparations were electrophoresed through 2% agarose and the fragments of 45 bp, 190 bp, 135 bp, and 70 bp from the mutant DNAs containing human 1, 2, 6, and 8 mutations, respectively, were eluted from the gel. Volumes of each fragment are collectively ligated to a gel-purified 3.7 kb EcoRI-SalI fragment from pBR322 with T4 DNA ligase and used to transform competent E. coli DH5 cells (BRL) as described by the supplier. A clone containing the mutations specified by all four mutant oligomers is selected by hybridization with radiolabeled probes prepared from each of the oligomers. The 140 bp KpnI-BamHI DNA fragment isolated from cleaved RF DNA of the human 3 mutant M13 clone is ligated to endonucleage cleavage products of this human 1-2-6-8 mutant DNA and transformed into DH5 competent cells to generate a clone with the human 1-2-3-6-8 mutations. BamHI-PstI digestion fragments of this latter clone are ligated to the BamHI-PstI digestion fragments of RF DNA from the human 4-5 M13-based clone and the ligation mixture is used to transform DH5 competent cells. A clone containing the human 1-2-3-4-5-6-8 mutations is selected by oligomer hybridization and the AFGF gene EcoRI-SalI DNA fragment of this recombinant plasmid is ligated to phosphatase-treated EcoRI-SalI-cleaved RF DNA of M13mp18 (BRL). Competent DH5 cells are transformed with this ligated DNA and the transformed cells are plated on JM105 host cells to generate an M13 clone. The single-stranded phage DNA of this clone was annealed with the human 7 oligomer and an M13 clone containing all the desired mutations was obtained following the procedure described above. The human aFGF clone is designated M13mp18-haFGF.

Pure AFGF in the absence of heparin becomes less active presumably due to the generation of incorrectly stabilized intramolecular disulfide bonds and aggregates formed by intermolecular disulfide bonds. The covalent disulfide bonds are formed between two cysteine residues either in two separate polypeptide chains, interchain disulfide bond, or in different positions within a single chain, intrachain disulfide bond. In the case of enzymatic oxidative iodination, the active molecules can be recovered by reduction with 20 Mm dithiothreitol in the presence of 3 M quanidinium chloride at a pH of about 9.1. The present invention utilizes site-directed mutagenesis for the specific substitution or deletion of amino acids capable of forming extraneous intramolecular or intermolecular covalent bonds and oxidation susceptable amino acids. Substitution as used herein refers to a deliberate change in the DNA base sequence of AFGF such that a desired amino acid is substituted for an undesired amino acid. The undesired amino acid may be one which forms unwanted covalent bonds, especially disulfide bonds, or one which is air-oxidizable either of which may decrease-the biological activity of the molecule. A deletion as used herein refers to a deliberate change in the DNA base sequence of AFGF resulting in the elimination of the unwanted amino acid. The primary amino acid associated with intramolecular and intermolecular covalent bond formation is cysteine while the amino acids which are oxidization prone include cysteine, methionine and tryptophan. The cysteine residue or residues may be replaced with any amino acid which will not form disulfide bonds. The prefered amino acid for the substitution of cysteine is serine. The oxidation prone amino acids are replaced with any amino acid which is oxidation resistant, this includes, but is not restricted to, alanine, valine, leucine and isoleucine.

The invention is contemplated to include site-specific mutations of one or more of the cysteine residues and any non-terminal methionine residue which could render native or recombinant AFGF less active or inactive due to the formation of incorrect intramolecular or intermolecular bonds or oxidative changes. The recombinant and native human and bovine protein contains two cysteine residues in common located at positions 16 and 83 and a methionine residue in common located at position 67 as defined by the native 140 amino acid form of both bovine and human AFGF. Bovine and human aFGFs each contain a third cysteine residue at positions 47 and 117, respectively. The common cysteine residues are the most likely to form a disulfide bond since the location of cysteine residues in disulfide bonds is highly conserved in homologous proteins. Thus the third cysteine residues that are in different locations in bovine and human aFGFs are very likely not found in disulfide linkages in the fully active proteins. It will be understood that the novel mutant aFGFs of the present invention will not only include the forms substituted at the non-common cysteine residues but also those that have all cysteines substituted or deleted, those in which any one or two of the cysteines have been substituted or deleted and those in which methionine has been substituted or deleted. The substitution or deletion of any one, especially the unique cysteine, all cysteines, two of the three cysteines or methionine in the human or bovine AFGF by site-directed mutagenesis may after the formation of unwanted intramolecular and intermolecular disulfide bonds and oxidized forms.

Site-specific mutagenesis is carried out on preferably bovine or human r-aFGF produced from genomic DNA, CDNA or by construction of genes for one or more of the microheterogeneous forms of the protein based on the microheterogeneous forms of AFGF from mammalian species including min. Genomic DNA is extracted from mammalian brain or pituitary cells and prepared for cloning by either random fragmentation of high molecular weight DNA following the technique of Maniatis et al., Cell 15: 687-701 (1978) or by cleavage with a restriction enzyme by the method of Smithies et al., Science 202: 1284-1289 (1978). The genomic DNA is then incorporated into an appropriate cloning vector, generally *E. coli* lambda phage, see Maniatis et al., Molecular Cloning, A Laboratory Manual, Cold Spring Harbor Laboratory, Cold Spring Harbor, New York (1982).

To obtain CDNA for AFGF, poly (A)-containing RNA is extracted from cells that express AFGF by the method of Aviv and Leder, Proc. Natl. Acad. Sci. 69: 1408-1412 (1972). The CDNA is prepared using reverse transcriptase and DNA polymerase using standard techniques, as described in Maniatis et al., Molecular Cloning, a Laboratory Manual, Cold Spring Harbor Laboratory, Cold Spring Harbor, New York (1982). The cDNA is tailed and cloned into an appropriate vector, usually pBR322, by a technique similar to that of Wensink, et al., Cell 3: 315-325 (1974).

The clonal genomic DNA or CDNA libraries are screened to identify the clones containing AFGF sequences by hybridization with an oligonucleotide probe. The sequence of the oligonucleotide hybridization probe is based on the determined amino acid sequence of AFGF. Maniatis et al., supra, Anderson and Kingston, Proc. Natl. Acad. Sci. USA 80: 6838-6842 (1983) and Suggs et al., Proc. Natl. Acad. Sci. USA 78: 6613-6617 (1981) describe various procedures for screening genomic and CDNA clones. The preferred procedure is to specifically point mutate the synthesized bovine and human genes as described above.

Site-specific mutagenesis is carried out on a human or bovine AFGF single-stranded bacteriophage recombinant clone, such as M13mp18-haFGF or M13mp19-baFGF following the procedures of Zoller, and Smith, Methods in Enzym. 100: 468-500 (1983), Norris et al., Nucleic Acids Res. 11: 5103-5112 (1983), and Zoller and Smith, DNA 3: -479-488 (1984). Three oligonucleotides for each species are designed to specify serine dodons in place of each of the cysteine codons of the human AFGF gene at positions 16, 83 and 117 and at positions 16, 47 and 83 for the bovine gene. An oligonucleotide is designed to specify a leucine codon in place of the methionine codon of the human or bovine AFGF at position 67. The human oligomers synthesized are shown in the following table with the mutated bases underlined.

TABLE XI

| |
|---|
| Cysteine 1 (16) 5' CCGTTAGAGG<u>A</u>GTAAAGAAGC 3' |
| Cysteine 2 (83) 5' GGAAAAGG<u>G</u>ACTCCTCG 3' |
| Cysteine 3 (117) 5' CCGCGTTTA<u>G</u>AGCTGCC 3' |
| Methionine (67) 5' CCATCAGTGTCCA<u>G</u>GGCAAGG 3' |

Similar oligomers are identified for the appropriate regions of the bovine AFGF gene and the specific mutations carried out as described below.

The human oligomers are phosphorylated and annealed individually to M13mp18-haFGF or M13mp19-baFGF single-stranded DNA. A second strand of DNA is synthesized using the annealed oligomer as primer. Each cysteine mutated gene is used to transform an appropriate host such as competent *E. coli* DH5 cells. The transformed cells are plated on a lawn of an acceptable host for the M13 virus such as *E. coli* JM105 cells. The transformed plaques are selected by hybridization with the appropriately labeled oligomer. Conditions of hybridization are optimized for each probe to prevent retention of hybrids containing single base changes. Single-stranded DNA is isolated from phage clones containing each of the cysteine-to-serine mutations for DNA sequence analysis using the method of Sanger et al., Proc. Natl. Acad. Sci. USA 74: 5463-5467 (1977). RF DNAs are prepared for each clone, cleaved with EcoRI and SalI and purified by agarose gel electrophoresis. The purified 440 bp inserts are individually ligated to the 2.7 kb EcoRI-SalI DNA fragment of the pKK2.7 tac promoter expression vector. The ligated DNAs are used to transform competent DH5 cells and clones containing DNA with the mutated cysteine codons are selected by hybridization to the appropriate oligomer. Each AFGF gene insert is sequenced by the method of Maxam and Gilbert, Methods in Enzymololgy 65: 499-560 (1980). The clones containing the single base change from the original human DNA are designated: pKK-haFGF (Ser 16), pKK-haFGF (Ser 83) and pKK-haFGF (Ser 117); while the bovine DNA; is designated pKK-baFGF (Ser 16), pKK-baFGF (Ser 47) and pKK-baFGF (Ser 83), for the location of the substitution in the protein.

Substitution of any two or all three of the cysteine residues is accomplished by multiple point mutations or by combining restriction fragments of either human or bovine recombinant wild-type and the (Ser 16), (Ser 47), (Ser 83) and (Ser 117) mutant synthetic genes, cloned in M13mp19 for bovine and M13mp18 for human, and subcloned in pKK2.7 as described above. It is to be understood that the multiple mutations can be carried out with either the bovine or human single mutation AFGF constructs as described above, however, the following illustration will include only human AFGF. The pKK-haFGF (Ser 16,32) and pKK-haFGF (Ser 16,32) recombinants are constructed by introducing the 0.23 Kb EcoRl-BamHl fragment of M13mp18 (Ser 16) into pKK2.7 followed by insertion of the 0.2 Kb BamHl-SalI fragments either from M13mp18 (Ser 83) or from M13mp18 (Ser 117). The pKK2.7 vector is modified to remove the BamHl site upstream of the tac promoter while leaving the BamHl site in the multicloning sequence. Following digestion with the corresponding restriction enzymes, subsequent ligation and transformation of an appropriate host, clones are selected and screened for those containing plasmids with the expected b molecular weight for the recombinants, about 3.1 Kb. An appropriate bacterial host may include, but is not limited to, *E. coli* DH5, JM105 or AB1899.

The mutant haFGF (Ser 16,83,117) is constructed by replacing the 0.13 Kb SphI-SalI fragment of pKK-haFGF (Ser 16,83), by the corresponding fragment of pKK-haFGF (Ser 117) that encodes for Ser instead of Cys in the 117 position. The 3 Kb SphI-SalI fragment of pKK-haFGF (Ser 16,83) is purified by preparative agarose gel electrophoresis, electroelution and ligated to the 0.13 Kb SphI-SalI fragment of pKK-haFGF (Ser 117) purified from a 5% polyacrylamide gel in the same way. The purified fragments are ligated and recombinants selected as described above.

The pKK-haFGF (Ser 83,117) mutant is constructed by replacing the 0.3 Kb PstI fragment of pKK-haFGF, the non-mutated form, with the fragment pKK-haFGF (Ser 16,83,117) that includes the codons for Ser instead of Cys at positions 83 and 117 using the above techniques. Transformants are analyzed by PstI-SalI digestion to determine the orientation of the ligated fragments. All genes are sequenced by the dideoxy method of Sanger et al., Proc. Natl. Acad. Sci. USA 74:5463-5467 (1977).

Expression of a mutated AFGF gene is accomplished by a number of different promoter-expression systems in a number of different host cells. It is desired and intended that there be included within the scope of this invention, the use of other host cells and promoter-expression systems for the expression of the intact mutated AFGF gene. The host cells include bacteria, yeast, insect, and mammalian cells. The antigens may also be expressed in viruses. Although the genes can be expressed in numerous procaryotic cells and various eucaryotic cells. The preferred host cell is *Escherichia coli*. The expression vectors which can be used for the expression of the mutated AFGF include, but are not limited to, pBR322, pPLa2311, pKC30, ptacl2, Igtll, CheY, pAS1, pLC24, pSB226, SV40 and pKK223-3 with pKK223-3 being preferred. *Escherichia coli* expression vectors generally allow the translation of a methionine residue attached to the first amino acid of the desired protein. It will be understood that the present invention includes not only mutant r-aFGF with a terminal methionine but also mutant r-aFGF which has had the terminal methionine removed following translation in such cell types as yeast cells, mammalian cells or bacterial cells. The expression vector may have included in the DNA sequence one or more additional cistrons which will enhance the expression of the AFGF gene, Schoner et al., Proc. Natl. Acad. Sci USA 83: 8506-8510 (1986). The preferred construct uses the *E. coli* tac promoter, a hybrid between regions of the trp promoter and the lac promoter as described by deboer et al., Proc. Nat. Acad. Sci. USA 80: 21-25 (1983). Plasmid pKK 223-3 (Pharmacia) which contains the tac promoter and rrnb RRNA transcription terminator was modified to remove the pBR322-derived SalI restriction enzyme site. The rrnb RRNA terminator has been shown to allow expression by strong promoters, Gentz et al., Proc. Natl. Acad. Sci. USA 78: 4936-4940 (1981); Brosius, Gene 27: 161-172 (1984).

The pKK223-3 plasmid DNA is cleaved with restriction enzymes to produce a 2.7 kb DNA fragment to generate clone pKK2.7. The synthetic AFGF gene is cleaved from its pBR322 vector and transferred to the pKK2.7 plasmid after restricting pKK2.7 with EcoRI and SalI. The resulting recombinant, shown in FIG. 1, is transformed into *E. coli* JM105 (Pharmacia) or DH5 (BRL) cells and expressed.

The preferred enhancing expression vector will contain a nucleotide sequence, the first cistron, upstream of the gene encoding the desired protein, the second cistron. The mutated AFGF will be the second cistron. The first cistron will generally contain a Shine-Dalgarno sequence upstream of the stop codon. An enhancing expression vector may contain, but is not limited to, the following nucleotide sequence:

AATTATGTATCGATTAAATAAGGAGGAAT
        TACATAGCTAATTTATTCCTCCTTATTAA
(pKK2.7)    (cistron 1,2 oligomers)    (aFGF)

which is an effective first cistron for enhancing the expression of wild-type or mutant AFGF. The first cistron is inserted into the appropriate pKK-haFGF construct at the EcoR1 site. The insertion results in the loss of the EcoR1 cloning site. The recombinant is transformed into an appropriate host cell such as those described above and expressed. This construct results in about a 10-fold increase in wild-type or mutant AFGF expression. The plasmids containing the enhancing expression vector are designated pKK2c-haFGF. The present invention is contemplated to include clones containing the enhancing expression vector such as; pKK2c-haFGF (Ser 16), pKK2c-haFGF (Ser 83), pKK2c-haFGF (Ser 117), pKK2c-haFGF (Ser 16,83), pKK2c-haFGF (Ser 16,117), pKK2c-haFGF (Ser 83,117), pKK2c-haFGF (Ser 16,83,117).

The mutated expression clones are grown at about 37° C. in an appropriate growth medium, which consists of about 1% tryptone, about 0.5% yeast extract, about 0.5% NaCl, about 0.4% glucose and about .50 µg/ml ampicillin. When the optical density at 550 nm reaches about 0.5, isopropyl-β-D-thiogalactopyranoside (IPTG) may be added to give a final concentration of about 1 mM and growth is continued at about 37° C. for up to about 24 hours. The cells from 1 liter of culture medium are harvested by centrifugation and resuspended in a washing buffer containing about 100 Mm phosphate and about 5 mg/ml EDTA. After the final resuspension about 0.1 mg/ml of lysozyme is added and the suspension is incubated with gentle shaking at about 30° C. for about 15 minutes. The cells are collected by centrifugation and resuspended in a disruption buffer containing about 100 Mm sodium phosphate at about pH 6.0, about 3 Mm EDTA, about 0.03 Mm N-p-toluenesulfonyl-L-phenyl-alanine chloromethyl ketone (TPCK), about 0.05 mM pepstatin A, about 0.05 mM phenylmethylsulfonyl fluoride (PMSF), about 0.05 Mm leupeptin and about 15 µg/ml bovine pancreatic trypsin inhibitor (BPTI). The cells are either immediately disrupted or frozen and stored at −70° C. and disrupted immediately after thawing by about two passages through a French pressure cell at about 20,000 psi at about 4° C. The supernatant fluid is collected following centrifugation and lyophilyzed.

The mutated aFGFs are purified to homogeneity by a three step chromatography process employing a cation exchanger matrix followed by a Heparin-Sepharose affinity matrix followed by reverse phase high performance liquid chromatography (HPLC). The lyophilyzed supernatant fluids are resuspended in phosphate buffer, about 100 mM, about pH 6.0 and added to a cation exchanger, preferably CM-Sephadex which has been equilibrated with the same buffer. The CM-Sephadex is added at a ratio of about 6.5 ml of settled resin per gram of protein. The resin is collected in a scintered glass funnel and washed three times with phosphate buffered saline, about 100 Mm. phosphate and about 150 Mm NaCl at a pH of about 6. The resin is resuspended in the same buffer, packed in a column, washed and eluted with about 600 mM NaCl buffer. Heparin-Sepharose is equilibrated with about 10 mM phosphate buffer, pH about 7.2 added to the eluate at a ratio of about 1 ml of settled resin per 1 mg of protein, gently shaken for about 1 hour at about 41 and the resin-protein complex collected in a funnel. The resin is resuspended in the same buffer and packed in a column at 1-2 column volume per hour. The column was washed with a buffer containing about 10 mM phosphate, pH about 7.2 and about 0.8 M NaCl and eluted with 1.5 M NaCl in the same buffer. Each protein was collected and further purified by reverse phase HPLC. Fractions are loaded on an HPLC reversed phase column, about C₃, equilibrated with about 10 mM trifluoroacetic acid (TFA) and eluted with a gradient of from about 0 to about 100% 4 Mm TFA, about 0–67% CH₃CN in about 30 minutes.

Mitogenic activity of the purified mutated recombinant aFGFs is determined by incorporation of ³H-thymidine into DNA by cell line fibroblasts, preferably BALB/C 3T3 A31 (American Type Culture Collection). Mutant proteins from plasmids pKK-haFGF (Ser 16) and pKK-haFGF (Ser 83) stimulated fibroblasts at a level equal to or lower than the non-mutated human AFGF. Mutant protein pKK-haFGF (Ser 117) showed a stimulatory activity that is higher than the non-mutated forms in the absence of hepar in.

A well controlled and very reproducible mitogenic assay is required to compare the relative specific mitogenic activities of wild-type haFGF and the Cys to Ser mutants. Confluent cultures of Balb/c 3T3 cells in serum free culture fluid were stimulated with consecutive two-fold dilutions over at least 3 log orders of AFGF concentration spanning the complete rise of the response from background through peak DNA synthesis. One stimulatory unit is calculated as the amount of AFGF per ml that generated a half maximal response. The specific mitogenic activity is the number of stimulatory units per mg of pure AFGF. The assay is further standardized by diluting stock solutions to about 50 µg aFGF/ml of TFA/CH₃CN, or less. The dilution eliminates any concentration effect so that different samples can be compared.

Conversion of the Cys 117, any two Cys or all three Cys residues to Ser results in a 7 to 20 fold increase of the specific activity of the protein in the absence of heparin. Even in the presence of heparin, all 4 multiple mutants are are more active than wild-type human r-aFGF with haFGF (Ser 83,117) being about 2.7-fold more active. Although heparin stimulates the activity of wild-type AFGF 20-fold, it potentiates the activity of the mutants by only about 3- to about 5-fold.

Conversion of either all, or of any two, of the three Cys residues of human AFGF to Ser results in a 7 to 20 fold increase of the specific activity of the protein in the absence of heparin. Even in the presence of heparin, all four multiple mutants are more active than non-mutated haFGF, with haFGF Ser (83,117) being nearly 3-fold more active.

Mutated recombinant AFGF is useful in promoting the repair or healing of, but not limited to, soft tissue wounds resulting from burns, cuts or lacerations, and cutaneous ulcerations along with musculo-skeletal wounds such as bone fractures, ligament and tendon tears, and inflammation of bursas and tendons. Tissue repair as used herein is defined as the regeneration of tissue following the stimulation of mesodermal, ectodermal or neuroectodermal derived cells by AFGF. Mutated r-aFGF is also useful in promoting the healing and regeneration of cartilage and cartilageneous tissue. Administration of mutated AFGF for soft tissue repair, including corneal tissue, will generally be by topical, subcutaneous, intravenous or intraocular application. Soft tissue includes all tissue except that associated with the musculo-skeletal system as described above. The novel peptides may be administered with or without heparin, preferably without heparin, about 0.1 to about 100 µg/cm²/day of this invention, protein, to the wound area either topically or subcutaneously about 1 to about 100 µg/cm³/day. The most preferred application range for topical administration is about 1 to about 10 µg/cm²/day.

Heparin is a sulfated glycosaminoglycan consisting of equal parts of the sugars D-glucosamine and D-glucuronic acid which are sulfated to varying degrees. It is commercially available in an unmodified form as well as in a solution form for direct therapeutic utilization. When heparin is administered with AFGF in topical or subcutaneous applications the preferred concentration is from about 3 times to about 30 times the amount (mass) of AFGF administered per day.

For musculo-skeletal and cartilage repair or healing, the mutated r-aFGF is preferably administered at the site of the injury either during surgery or by injection. Surgical implantation of slow-release forms of the mutated AFGF will allow for a continued release of the growth factor for a prolonged period of time. Methods of formulation ok mutated AFGF for slow release are known in the art. Dosage levels for musculo-skeletal healing will be about 10 to about 100 µg/cm³/day.

Mutant r-aFGF is furthermore useful in promoting the facilitation of in vivo vascular tissue repair, such as blood vessel growth (angiogenesis), and vessel repair (such as the replacement of damaged endothelial cells) and in stimulating endothelial cell growth on appropriate substrates for the production of blood vessels for implantation. In vivo angiogenesis activity of the novel mutant r-aFGF peptides is accomplished by the internal administration such as subcutaneously, of about 1 to 1000 µg/cm³/day with the more preferred amount of about 10 to about 100 µg/cm²/day. The preferred application range for surface repair is about 100 ng to about 100 µg/cm²/day with the most preferred application range being about 1 to about 10 µg/cm²/day. Large vessel repair is accomplished by a single dose of about 0.1 to about 100 ng/cm³ or by continuous infusion of about 1 to about 1000 pg/cm³/day. In vitro growth of Endothelial cells on appropriate substrates for the production of blood vessels is accomplished by the administration of about 1 to about 10 ng/ml/day.

Mutant r-aFGF is also useful in the in vivo induction of plasminogen activator by vascular endothelial cells for the treatment of thrombotic attacks. Thrombotic attacks result form the formation of thrombi within blood vessels which may result in thrombotic strokes, deep vein thrombosis, myocardial infarction and other medical conditions which give rise to necrosis of tissues and often times death of the patient. Digestion of preformed clots and the prevention of further clot formation can be mediated by mutant r-aFGF thereby enhancing the treatment of thrombotic attacks. Pretreatment with mutant r-aFGF may also be used to prevent the formation of clots in animals, including man, which are at high risk for clot formation. The desirable dosage range of mutant r-aFGF for the treatment of thrombotic attack is about 10 µg-10 mg/kg/day.

Mutated and wild-type r-aFGF is also useful in promoting central and peripheral nerve tissue repair including the maintenance and stimulation of hippocampal neurons and neurons that are damaged or destroyed in Alzheimer's disease and motor and sensory neurons whose destruction causes paralysis. Damaged nervous tissue may be stimulated by mutated or wild-type AFGF to produce additional neurons by mitosis of neuroblasts to re-populate the damaged nerves in the area and to promote neurite outgrowth from neurons. The peptides may be administered as described for wound healing of either soft tissue or musculo-skeletal tissue.

For topical application, various pharmaceutical formulations are useful for the administration of the active compound of this invention. Such formulations include, but are not limited to the following: ointments such as hydrophilic petrolatum or polyethylene glycol ointment; pastes which may contain gums such as xanthan gum; solutions such as alcoholic or aqueous solutions; gels such as aluminum hydroxide or sodium alginate gels; albumins such as human or animal albumins; collagens such as human or animal collagens; celluloses such as alkyl celluloses, hydroxyalkyl celluloses and alkylhydroxyalkyl celluloses, for example methylcellulose, hydroxyethyl cellulose, carboxymethyl cellulose, hydroxypropyl methylcellulose, and hydroxypropyl cellulose; poloxamers such as Pluronic ® Polyols exemplified by Pluronic F-127; tetronics such as tetronic 1508; and alginates such as sodium aliginate. The pharmaceutical formulations will include one or more of the mutated AFGF compounds in amounts of about 0.1 to about 100 μg/ml.

For non-topical application the mutant r-aFGF is administered in combination with pharmaceutically acceptable carriers or diluents such as, phosphate buffer, saline, phosphate buffered saline, Ringer's solution, and the like, in a pharmaceutical composition, according to standard pharmaceutical practice.

The ability of mutated AFGF to stimulate division in various cell types including fibroblasts, vascular and corneal endothelial cells and the like makes these peptides useful as pharmaceutical agents. These compounds can be used to treat wounds of mammals including humans by the administration of the novel mutated r-aFGF to patients in need of such treatment..

The following examples illustrate the present invention without, however, limiting the same thereto.

EXAMPLE 1

Oligonucleotide Synthesis

Oligonucleotides were synthesized according to the technique described by matteucci and Caruthers, J. Am. Chem. Soc. 103: 3185-3191 (1981); Beaucage and Caruthers, Tetrahedron Letters 22: 1859-1862 (1981). The base sequences of the synthesized oligonucleotides are shown in Tables VII, IX and XI.

EXAMPLE 2

Assembly of the AFGF Gene

The bovine oligonucleotides from Example 1 were assembled as two separate units, the N-terminal half (231 bp) and the C-terminal half (209 bp). The two halves were then combined for the intact synthetic gene, see Table VI. Initially the oligonucleotides were kinased in the following reaction mixture: 70 mM Tris pH 7.6, 5 mM DTT, 10 mM MgCl$_2$, 33 μM ATP, 0.3 units T4 polynucleotide kinase per μl, and 2.5 pmole oligonucleotide per μl. The mixture was incubated 1.5 hours at 37° C. and then an additional hour after supplementing the mixture with 0.2 units/μl kinase and ATP to give a concentration of 100 mM. For radioactive labelling, the initial mixture contained 37 nci/μl of [μ-$^{32}$P]-ATP.

The annealing and ligations were done in two separate reactions. In each reaction, 100 pmole of each of the eight oligonucleotides were added. In one reaction the oligonucleotides which make up one strand of the C-terminal or N-terminal half gene were kinased with the exception of the most 5' oligonucleotide. In the second reaction the oligonucleotides which make up the opposite strand were kinased, again with the exception of the most 5' oligonucleotide. Thus, in each reaction 3 oligonucleotides were kinased and 5 were not. When kinased oligonucleotides were used, 1 pmole of the $^{32}$P-labelled oligonucleotide was also added for later identification of the products. Each reaction contained 200 pl with 70 Mm Tris pH 7.6, 5 Mm DTT, 10 Mm mgCl$_2$ and 30 μM ATP. The oligonucleotides were annealed by heating to 90° C. for 4 minutes, then immediately transferring the reaction to 60° C. and allowing it to cool slowly to 30° C. Ligation was done in 400 pl containing 60 Mm Tris pH 7.6, 10 Mm DTT, 10 mM MgCl$_2$, 1 mM ATP, and 0.03 units T4 DNA ligase per μl by incubating at 20° C. for 1.5 hours.

Polyacrylamide gel electrophoresis was used to purify the ligated oligonucleotides. The ligated oligonucleotides were precipitated with ethanol, redissolved in 20 μl of 80% formamide, 50 mM TRIS-borate pH 8.3, 1 Mm EDTA, 0.1% (w/v) xylene cyanol, and 0.1% (w/v) bromophenol blue. Each sample was heated at 90° C. for 3 minutes and electrophoresed in a 10% urea-polyacrylamide gel at 75 watts for 5 hours. The oligonucleotide bands were visualized by exposing the gel to X-ray film.

The 231 base bands of each reaction for the N-terminus were cut out of the gel, combined, and eluted at 4° C. in 1 ml of 0.5 M ammonium acetate, 1 mM EDTA pH 8. The eluted. DNA was precipitated with ethanol and redissolved in 30 μl of 70 Mm Tris pH 7.6, 5 mM DTT, and 10 Mm MgCl$_2$. The 209 base bands of the C-terminus were eluted in the same manner.

The gel purified oligonucleotides were annealed prior to transformation by heating to 90° C. for 4 minutes and slow cooling to 20° C. Assuming a 5% recovery from the initial starting oligonucleotides, 300 fmole and 100 fmole of recovered annealed 231 bp oligonucleotides were each ligated to 100 fmole of agarose gel purified 3.9.kb EcoRI-BamHI pBR322 fragment DNA in 20 μl of 25 Mm Tris pH 7.8, 1 mM DTT, 10 mM MgCl$_2$, 0.4 mM ATP, with 1 unit T4 DNA ligase for 1 hour at 20° C. The annealed 209 bp oligonucleotides were ligated to agarose purified 3.9 kb BamHI-SalI pBR322 fragment DNA under the same conditions as the 231 base pair fragments. The ligation reactions were diluted 1:5 in H 0 and 1 μl of dilution was used to transform 20 μl of competent E. coli RRi cells (BRL) as described by the supμlier. The transformants were selected for growth in ampicillin and screened for the presence of the 231 bp EcoRI-BamHI or the 209 bp BamHI-SalI insert by restriction analysis of mini-lysate μlasmid preparations.

The DNA sequence of clones containing the appropriate sized inserts was determined using the chemical DNA sequence techniques of Maxam and Gilbert, Proc. Natl. Acad. Sci. USA 74: 560-564 (1977). Since none of the 231 bp clones had the correct sequence, a clone containing the correct sequence was prepared as follows. One clone with the correct sequence between the KpnI and BamHI sites was cleaved with KpnI and with SalI, which cleaves in the pBR322 vector. The 400 bp band was gel purified and ligated to the 3.8 kb KpnI-SalI band of a second clone containing the correct sequence from the EcoRI site to the KpnI site of the AFGF gene insert. After transformation, a resulting clone was sequenced to ensure the desired sequence had been obtained.

Since a clone containing the correct 209 bp sequence was obtained, no further manipulation of these clones was required. The final full-length aFGF synthetic gene was cloned by cleaving the N-terminal half clone with BamHI and SalI, treating with alkaline phosphatase, and ligating this to the gel purified 209 bp BamHI-SalI insert of the C-terminal half clone. This ligated material was used to transform competent RR1 cells as before.

EXAMPLE 3

Mutagenesis of the Bovine AFGF Gene to the Human AFGF Gene

To facilitate the mutagenesis of the bovine aFGF gene, the synthetic gene from Example 2 was transferred to M13MP19, a single-stranded DNA bacteriophage vector. Standard mutagenesis procedures were used as reported by Zoller and Smith, Methods in Enzymology, 100: 468–500 (1983); Norris et al., Nucleic Acids Research, 11: 5103–5112 (1983); and Zoller and Smith, DNA, 3: 479–488 (1984). The bovine pKK-aFGF plasmid was cleaved with EcoRI and SAII and the resulting 440 bp fragment was agarose gel purified as in Example 2. Vector M13mp19 RF DNA (BRL) was cleaved with the same two endonucleases and the ends were subsequently dephosphorylated in 100 µl of 10 mM Tris pH 8.0 buffer with 100 units of bacterial alkaline phosphatase. A ligation was performed using 50 ng of the treated vector DNA and 12 ng of the AFGF gene fragment DNA in 10 µl of 25 mM Tris pH 7.8, 10 Mm MgCl$_2$, 1 mM DTT, 0.4 mM ATP, with 2 units of T4 DNA ligase for 16 hours at 4° C. The reaction mixture was diluted 1:5 in H$_2$O and 1 µl of dilution was used to transform 20 µl of competent E. coli DH5 cells (BRL) as described by the supµlier. The cells were plated with E. coli JM105 (Pharmacia) host cells in 0.03% X-gal and 0.3 Mm IPTG; after incubation at 37° C. colorless plaques were isolated. One phage clone containing the bovine AFGF gene was selected, M13MP19-baFGF.

Eight oligonucleotides were designed to specify the human sequence and synthesized, see Table IX. Oligomer 8 contains an additional mutation in which thymine at site 386 in the bovine gene is repµlaced by cytosine in the human gene. This mutation allows the incorporation of a restriction site without altering the human AFGF amino acid sequence.

The human oligomers 1, 2, 3, 4, 6, and 8 were phosphorylated and 15 pmoles of each were annealed individually to 0.5 pmole of M13mp19-baFGF single-stranded phage DNA in 10 µl of 20 mM Tris pH 7.5, 10 mM MgCl$_2$, 50 mM NaCl, 1 mm DTT for 10 minutes at 65° C. followed by 10 minutes at 23° C. Closed-circular double-stranded molecules were then prepared in 20 µl of 20 mM Tris pH 7.5, 10 Mm mgcl$_2$, 25 mM NaCl, 5.5 Mm DTT, 0.5 Mm ATP, 0.25 mM dATP, 0.25 mMd CTP, 0.25 Mm DGTP, 0.25 Mm DTTP, using 1 unit of T4 DNA ligase and 2 units of DNA polymerase: I klenow fragment by incubation at 15° C. for 17 hours. The preparations were each used to transform competent JM105 cells and the resulting transformant plaques were selected by hybridization with the appropriate oligomer which had been radio-labeled using $^{32}$P-ATP and polynucleotide kinase. The conditions of hybridization were optimized for each probe to prevent formation of hybrids containing single base changes. Single-stranded DNA was isolated from the phage clone containing the human oligomer 4 mutations and the above procedure was repeated using the human oligomer 5 to generate a clone containing both the oligomer 4 and 5 mutations.

In the following procedures the bovine-to-human sequence mutations in these M13-based clones were combined into one pBR322-based clone. RF DNAs were prepared from clones containing the base changes specified by human oligomers 1, 2, 6, and 8. The DNA of the human 1 mutant clone was cleaved with EcoRI, the ends were dephosphorylated with bacterial alkaline phosphatase, and the DNA was cleaved with HindIII. The human 2 mutant DNA was cleaved with HindIII, treated with phosphatase, and then cleaved with BamHI. The human 6 mutant DNA was cleaved with BamHI, phosphatase treated, and subsequently cleaved with ApaI. Likewise, the human 8 mutant DNA was cleaved with ApaI, the ends were dephosphorylated, and the DNA was cleaved with SalI. These four DNA preparations were electrophoresed through 2% agarose and the fragments of 45 bp, 190 bp, 135 bp, and 70 bp from the mutant DNAs containing human 1, 2, 6, and 8 mutations, respectively, were eluted from the gel. Approximately 60 fmoles of each fragment were collectively ligated to about 60 fmoles of a gel-purified 3.7 kb EcoRI-SalI fragment from pBR322 in 5 µl of 25 Mm Tris pH 7.8, 10 mM MgCl$_2$, 1 Mm DTT, 0.4 mM ATP, with 1.5 units of T4 DNA ligase for 16 hours at 12° C. The reaction mixture was diluted 1:5 in H$_2$O and 1 µl of dilution was used to transform 20 µl of competent E. coli DH5 cells (BRL) as described by the supplier. A clone containing the mutations specified by all four mutant oligomers was selected by hybridization with radiolabeled probes prepared from each of the oligomers. The 140 bp KpnI-BamHI DNA fragment isolated from cleaved RF DNA of the human 3 mutant M13 clone was ligated to endonuclease cleavage products of this human 1-2-6-8 mutant DNA and transformed into DH5 competent cells to generate a clone with the human 1-2-3-6-8 mutations. BamHI-PstI digestion fragments of this latter clone were ligated to the BamHI-PstI digestion fragments of RF DNA from the human 4-5 M13-based clone and the ligation mixture was used to transform DH5 competent cells. A clone containing the human 1-2-3-4-5-6-8 mutations was selected by oligomer hybridization and the AFGF gene EcoRI-SalI DNA fragment of this recombinant µlasmid was ligated to phosphatase-treated EcoRI-SalI-cleaved RF DNA of M13mµl8 (BRL). Competent DH5 cells were transformed with this ligated DNA and the transformed cells were plated on JM105 host cells to generate an M13 clone. The single-stranded phage DNA of this clone was annealed with the human 7 oligomer and an M13 clone containing all the desired mutations was obtained following the procedure described above. RF DNA was prepared from this clone and cleaved with EcoRI and SalI. The resulting 440 bp band was gel purified and ligated to the 2.7 kb EcoRI-SalI DNA fragment of the pKK2.7 tac promoter expression vector. This DNA was used to transform competent DH5 cells thus generating the human pKK-aFGF expression clone used for production of the human form of AFGF.

EXAMPLE 4

Mutagenesis of the Cysteine Codons of the AFGF Gene

A human AFGF single-stranded bacteriophage recombinant clone, M13mp18-haFGF, from Example 3 was mutagenized using procedures reported by Zoller and Smith, *Methods in Enzymology*, 100: 468–500 (1983); Norris et al., *Nucleic Acids Research*, 11: 5103–5112 (1983); and Zoller and Smith, *DNA*, 3: 479–488 (1984). Three oligonucleotides were designed to specify serine codons in place of each of the cysteine codons of the human AFGF gene at positions 16, 83, and 117. The oligomers synthesized are shown in Table XI with the mutated bases underlined.

The oligomers were phosphorylated and 15 pmoles of each were annealed individually to 330 ng of M13mp18-haFGF single-stranded DNA in 10 ul of 20mm Tris pH 7.5, 10 mM $MgCl_2$, 50 mM NaCl, and 1 Mm DTT for 10 minutes at 65° C. followed by 10 minutes at 23° C. A second strand of DNA was synthesized using the annealed oligomer as primer in 20 ul of 20 Mm Tris pH 7.5, 10 Mm $MgCl_2$, 25 mM NaCl, 5.5 Mm DTT, 0.5 mM ATP, 0.25 mM DATP, 0.25 DCTP, 0.25 mM DGTP, 0.25 mM DTTP, using 3 units of T4 DNA ligase and 0.4 units of DNA polymerase I klenow fragment by incubation at 12° C. for 17 hours. The three preparations were each diluted 1:5 in $H_2O$ and 1 ul of dilution was used to transform 20 ul aliquots of competent *E. coli* DH5 cells (Bethesda Research Labs) as described by the supµlier. The transformed cells where plated with a lawn of *E. coli* JM105 cells which act as host cells for the M13 virus. The resulting transformant plaques were selected by hybridization with the appropriate oligomer which had been radiolabeled using $^{32}$P-ATP and polynucleotide kinase. The conditions of hybridization were optimized for each probe to prevent retention of hybrids containing single base changes.

Single-stranded DNA was isolated from phage clones containing each of the cysteine-to-serine mutations for DNA sequence analysis using the dideoxynucleotide chain termination method of Sanger. et al., *Proc. Natl. Acad. Sci. USA* 74:5463–5467 (1977). RF DNAs were then prepared from three clones, each containing one of the specified mutations, and after cleavage with EcoRI and SalI the released FGF gene inserts were isolated by agarose gel electrophoresis. The purified 440bp inserts were each ligated to the 2.7kb EcoRI-SalI DNA fragment of the pKK2.7 tac promoter expression vector in 10 ul of 25mM Tris pH 7.8, 10 Mm $MgCl_2$, 1 mM DTT 0.4 mM ATP, with 3 units of T4 DNA ligase for 2 hours at 14° C. The ligated DNAs were used to transform competent DH5 cells and clones containing DNA with the mutated Cys codons were selected by hybridization to the appropriate oligomer. The FGF gene insert in the µlasmid DNA of these clones was sequenced completely by the chemical method of Maxam and Gilbert, *Methods in Enzymology* 65:499–560 (1980). One clone contained only the single base change from the original human aFGF expression clone generating a serine codon in place of a cysteine codon at position 83 and is designated as pKK-haFGF(Ser 83).

The clones containing each of the other two cysteine-to-serine mutations also contained additional non-specified changes. In order to generate the desired single base mutants the following ligations and transformations were performed. The 410bp HindIII-derived DNA fragment of the clone with the serine codon at position 16 was isolated and ligated to the 2.7kb HindIII-derived fragment of the original pKK-haFGF expression clone. The 230bp NcoI-SalI-derived DNA fragment of the clone containing the serine codon at position 117 was isolated and ligated to the 2.9kb NcoI-SalI-derived fragment of pKK-haFGF. Each of these ligated samples was used to transform competent DH5 cells; hybridization and sequencing techniques were used to identify the other two desired single base mutants designated pKK-haFGF(Ser 16) and pKK-haFGF(Ser 117). These three clones were used for production of the Ser 16, Ser 83, and Ser 117 forms of the human AFGF.

Site-directed mutants of human AFGF with two or three cysteine (cys) residues converted to serine (Ser) residues were-constructed by combining restriction fragments of the non-mutated wild-type and the Ser (16), Ser (83) and Ser (117) mutant synthetic genes, have been cloned in pKK2.7 and subcloned in M13mp18, as described above. The pKK-haFGF (Ser 16,83) and pKK-haFGF (Ser 16,117) recombinants were constructed first by introducing the 0.23 Kb EcoRI-BamHl fragment of M13mp18 (Ser 16), that includes the codon for Ser 16, into pKK2.7 followed by insertion of the 0.2 Kb BamHl-SalI fragments either from M13mµl8 (Ser 83) or from M13mp18 (Ser 117). Since the pKK2.7 vector contains two BamHI sites, one in the multicloning sequence and the second one upstream of the tac promoter, a modified pKK2.7 vector, in which the second upstream BamHI site was eliminated, was used in these constructions. After digestion with the corresponding restriction enzymes, subsequent ligation and transformation of AB1899 competent cells (*E. coli* Genetic Stock Center), ampicillin resistant clones were selected and screened for those containing plasmids with the expected molecular weight for the recombinants (3.1 Kb).

The mutant haFGF (Ser 16,83,117) was constructed by reµlacing the 0.13 Kb SphI-SalI fragment of pKK-haFGF (Ser 16,83), by the corresponding fragment of pKK (Ser 117) that encodes for Ser instead of Cys in position 117. The 3 Kb SphI-SalI fragment of pKK (Ser 16,18) was purified by preparative agarose gel electrophoresis, electroelution and ligated to the 0.13 Kb SphI-SalI fragment of pKK (Ser 117) purified from a 5% polyacrylamide gel in the same way. The purified fragments were ligated and recombinats were selected for ampicillin resistance after transformation of AB1899 cells.

For construction of pKK-haFGF (Ser 83,117), the 0.3 Kb PstI fragment of pKK haFGF was replaced with the same fragment of pKK-haFGF (Ser 16,83,117) that includes the codons for Ser instead of Cys at positions 83 and 117 using basically the same strategy. AB1899 transformants selected for ampicillin resistance were analyzed by PstI-SalI digestion to determine the orientation of the ligated fragments. All mutant genes were sequenced by the dideoxy method using the Sequence kit of USB Corp.

EXAMPLE 5

Expression of the Synthetic Bovine AFGF Gene

The intact AFGF genes from Example 4 were incorporated into a modified pKK223-3 plasmid. The pKK223-3 plasmid (Pharmacia) contains the tac promoter which is a hybrid between regions of the trp promoter and the lac promoter, deboer et al., *Proc. Natl*

Acad. Sci. USA 80: 21-25 (1983). This plasmid also contains the rrnb RRNA transcription terminator, a strong terminator sequence found to allow expression from strong promoters, Gentz et al., Proc. Natl. Acad. Sci. USA 78: 4936-4940 (1981); Brosius, Gene 27: 161-172 (1984). The pKK223-3 plasmid was modified to remove the pBR322-derived SalI restriction enzyme site. This was accomplished by cleaving the pKK223-3 plasmid DNA with NdeI and NarI, blunt-ending the DNA fragment with Klenow DNA polymerase, and recircularizing the 2.7 kb DNA fragment to generate clone pKK2.7. The synthetic AFGF gene was then cleaved from its pBR322 vector and transferred to pKK2.7 after restricting this expression vector with EcoRI and SalI. This construction positions the initiating methionine of the synthetic gene 11 bases downstream of the Shine-Dalgarno ribosome binding site. The resulting recombinant vectors, as exemplified by FIG. 1, were transformed into E. coli JM105 cells and also into E. coli DH5 cells.

The expression clones were grown at 37° C. in LB broth (1% tryptone, 0.5% yeast extract, 0.5% NaCl) containing 0.4% glucose and 50 µg/ml ampicillin. When the optical density at 550 rim reached 0.5, IPTG was added to give 1 Mm and growth was continued at 37° C. for 3 hours. The cells were harvested by centrifugation at 10,000×g for 20 minutes and the cells from 1 liter of culture were resuspended in glycerol/phosphate buffered saline 1:1 and quickly frozen in a dry ice/ethanol bath and stored overnight at −70° C.

EXAMPLE 6

Enhanced Expression Vector

Enhanced levels of expression for the mutated forms of AFGF of Example 4 were provided by modification of the expression vector of Example 3 to introduce an additional cistron upstream of the AFGF encoding sequence. Two oligonucleotides were synthesized with the sequences as shown at page 40. When annealed these oligomers supply 5' extensions of 4 bases which are complementary to the extensions provided by EcoRl cleavage, a 7 codon open reading frame following the ATG translation initiation codon and preceding a TAA stop codon, and an additional Shine-Dalgarno ribosome binding site located within the open reading frame upstream of the stop codon. Using 1 pmole of each oligomer, the oligomers were annealed together in 20 µl of DNA ligase buffer by heating to 70° C. for 10 minutes and slow cooling. The annealed mixture, 0.3 pmole, was ligated to 0.1 pmole of EcoRl-cleaved pKK-haFGF plasmid DNA in a final volume of 25 µl containing 3 units of T4 DNA ligase (Pharmacia) for 2.5 hours at 14° C. The ligated DNA, 5 ng, was used to transform competent E. coli JM105 cells. The transformants were screened by restriction analysis, as the EcoRl site is lost by this insertion, and by immunoblot analysis. The expression vector of one clone, which demonstrated higher levels of FGF production, was sequenced by the chemical technique of Maxam and Gilbert, supra, to verify the correct insertion of the new cistron sequences. Subsequently, this high expression pKK2c-haFGF vector was transfered to E. coli DH5 by transformation procedures.

In order to express the haFGF (Ser 117) mutant gene, for example, in this high expression vector, the 0.23 kb NcoI-SalI fragment of pKK-haFGF (Ser 117) was ligated to the 2.5 kb NcoI-SalI fragment of pKK2c-haFGF and transformed into competent cells. The other mutated haFGFs were transferred to the two cistron high expression vector in a similar manner, replacing appropriate restriction fragments containing the wild-type sequences of pKK2c-haFGF with the analogous restriction fragments of the mutated haFGF.

EXAMPLE 7

Extraction and Purification of Mutated AFGF

The frozen cells from Example 5 were thawed and resuspended in a quantity sufficient to make 50 ml with 100 mM phosphate buffer, pH 7.2, 5 mg/ml EDTA and the cells were collected by centrifugation at 28,000×g for 5 minutes. The cells were washed a second time, collected by centrifugation and resuspended in 50 ml of the same buffer. The extinctions of the three mutant strain suspensions at 660 nm were strain pKK-haFGF(Ser 117), 103; strain pKK-haFGF(Ser 16), 108; strain pKK-haFGF(Ser 83) 59. Each sample received 0.1 mg/ml of lysozyme and was incubated for 15 minutes with gentle shaking at 30° C. The cells were collected by centrifugation and resuspended in 50 ml of breaking buffer consisting of 100 mM phosphate; pH 6.0; 3 mM, EDTA; 0.05 mM, TPCK, 0.05 mM, Pepstatin A, 0.05 mM, Leupeptin and 15 µg/ml BPTI. Each cell suspension was kept at 40° C. and broken by two passages through a previously cooled French pressure cell at 20,000 psi at 4° C. The disrupted cell suspensions were centrifuged for 15 minutes at 15,000 rpm in a SS-34 Sorvall rotor and for 60 minutes at 45,000 rpm in a 70 Ti rotor in a Beckman ultracentrifuge at 4° C. The supernatant fluid was collected, the extinctions at 280 nm for a 55 ml volume were determined: pKK-haFGF(Ser 117), 44; pKK-haFGF(Ser 16), 40 and pKK-haFGF(Ser 83), 23 and the samples were frozen at −70° C.

The supernatant fluids were thawed by the addition of 200 ml of 100 Mm phosphate buffer, pH 6.0, containing CM-Sephadex at a ratio of 6.5 ml of settled resin per gram of protein (assuming absorbance through a 1 cm path of a 1 mg/ml protein solution is 1.0). The sample was collected in a scintered glass funnel and washed three times with 200 ml of 100 Mm phosphate buffer containing 150 mM NaCl at a pH of 6.0. The resin cake was resuspended in 200 ml of the same buffer, packed in a column at 12 ml×hr$^{-1}$per cm$^2$ crossectional ARGA and washed at the same flow rate with 150 mM phosphate buffer containing 600 Mm NaCl. The fractions containing the protein eluted with the 600 mm NaCl buffer were pooled, the pH adjusted to 7.2 and the conductivity adjusted with deionized water to 10 µS×cm$^{-1}$. Heparin-Sepharose (freshly prepared) equilibrated with 10 mM phosphate pH 7.2 (conductivity 1.3 µS×cm$^{-1}$) was then added at a ratio of 1 ml of settled resin per mg of protein (using the same assumed extinction coefficient as above), the suspension gently shaken for one hour at 4° C., and the resin collected in a funnel, resuspended in the same buffer and packed in a column at 1-2 column volume per hour. The packed column was washed with 10 mM phosphate, 0.8 M NaCl pH 7.2 at the same flow rate until the extinction of the eluate at 280 nm decreased to a steady value, to within 0.01 optical absorbance units above the elution buffer and then the buffer changed to 10 mM phosphate, 1.5 M NaCl pH 7.2. The fractions containing the protein eluted with the 1.5 M buffer (monitored by the extinction at 280 nm) were pooled together and loaded in a C$_3$ reversed phase HPLC column equilibrated with 10 mM TFA and eluted with a gradient from 0-67% CH₃CN in 30 minutes.

The purification data of the mutant strains is shown below:

pKK-haFGF(Ser 16)

Fractions 25-31 eluted from the CM-Sephadex column with the 0.6 M NaCl buffer in a total volume of 24 ml and a protein content of 3.5 mg were made 125 ml with deionized water (final conductivity: 7 mS/cm) and 4 ml of heparin-Sepharose added. The column was run at 6 ml/h. Fractions 55-57 eluted with 1.5 M NaCl, were injected on-the $C_3$ column. From this column a major peak was collected with a protein content of 80 µg.

pKK-haFGF(Ser 83)

Fractions 19-33 eluted from the CM-Sephadex column with the 0.6 M NaCl buffer in a total volume of 40 ml and a protein content of 4.0 mg were made 150 ml with deionized water (final conductivity: 10 mS/cm) and 4 ml of heparin-Sepharose added. The column was run at 6 ml/h. Fractions 40-44, eluted with 1.5 M NaCl, were injected in the $C_3$ column. From this column a major peak was collected with a protein content of 80 µg.

pKK-haFGF(Ser 117)

Fractions 19-33 eluted from the CM-Sephadex column with the 0.6 M NaCl buffer in a total volume of 57 ml and a protein content of 11.4 mg were made 250 ml with deionized water (final conductivity: 12 mS/cm) and 10 ml of heparin-Sepharose added. The column was run at 11 ml/h. Fractions 59-62, eluted with 1.5 M NaCl, were injected in the $C_3$ column. From this column a major peak was collected with a protein content of 614 µg.

The protein products of the multiple mutants were purified by the same procedures. All forms of aFGF, recombinant wild-type and the mutants were highly purified since only single 16 kDa bands were seen following reduction and electrophoresis in SDS 15% polyacrylamide gels at loads 100-fold above the threshold of detection.

EXAMPLE 7
Biological Activity of Mutated AFGF

Biological activity of the purified r-aFGF from Example 6 was evaluated using a fibroblast mitogenic assay modified from Thomas et al., J. Biol. Chem. 225: 5517-5520 (1980). BALB/c 3T3 A31 fibroblasts (American Type Culture Collection) were plated at $3 \times 10^4$ cells per 100 µl per well in 96-well culture dishes in culture media containing 10% heat-inactivated calf serum and incubated in 7% $CO_2$ (pH 7.35±6.05). The cells became fully quiescent by replacing the media with 1.0% heat-inactivated calf serum 6 and again 24 hours later. At 55 hours after plating, 10 µl of test sample with or without 5 pg of heparin and 0.11 µg of dexamethasone were added, at 70 hours each well was supplemented with 0.2 µCi of [methyl-³H]-thymidine (20 Ci/mmole, New England Nuclear) and 0.3 µg of unlabeled thymidine (Sigma), and at 95 hours the cells were processed for determination of radiolabel incorporated into DNA. Each dose-response point was the average of four determinations. The results of Ser-117 Mutant, the only mutant form showing activity equal to or greater than wild type, are shown in the following table:

TABLE XII

Mitogenic Responses of BALB/c 3T3 Fibroblasts to Mutated aFGF

| Dose (amt/ml) | Wild type −heparin | Wild type +heparin | Ser-117 Mutant −heparin | Ser-117 Mutant +heparin |
|---|---|---|---|---|
| 3.16 pg | 1449 | 724 | 2055 | 883 |
| 10.0 pg | 1917 | 914 | 2662 | 1255 |
| 31.6 pg | 1547 | 1007 | 3076 | 2748 |
| 100 pg | 2263 | 2498 | 4833 | 8067 |
| 316 pg | 2647 | 14945 | 11505 | 44193 |
| 1.00 ng | 3975 | 54516 | 22869 | 66778 |
| 3.16 ng | 6400 | 68447 | 40487 | 60306 |
| 10.0 ng | 12665 | 61294 | 54163 | 56326 |
| 31.6 ng | 21843 | 56552 | 70670 | 59854 |
| 100 ng | 44744 | 66816 | 66802 | 63856 |

The 4 titration curves are compared at their half-maximal rise. The WT in the absence of heparin does not reach a peak so the same peak magnitude is assumed as seen for the other 3 peaks and the half-maximal value extrapolated.

TABLE XIII

Comparison of Concentrations Necessary for Half Maximal Stimulation

| Sample | Heparin | Conc. of ½ maximal stimulation |
|---|---|---|
| WT | − | 66 ng/ml |
| | + | 0.56 ng/ml |
| Ser-117 Mutant | − | 2.3 ng/ml |
| | + | 0.20 ng/ml |

All dilutions were prepared from a stock solution containing 1.51 mg/ml of purified reactants. The Ser-117 mutant is at least as active as the wild type in the presence of heparin. The activity of the wild type is about 10-fold more dependent on heparin than the mutant consequently 90% of the heparin dependence of WT AFGF is eliminated in the Ser-117 mutant.

The mitogenic assay used to evaluate biological activity was modified so that mutated and wild-type AFGF could be compared. Heat-inactivated calf serum was replaced with 1% insulin-selenium-transferin (ITS), 0.4 gm L-histidine, 50 µl of 1 M ethanolamine, 1.25 gm bovine serum albumin with 5.35 mg of linoleic acid per liter of 75% DMED, 25% Ham's F12 containing both penicillin-streptomycin and L-glutamine as described above. Full dose-response assays were done as described above at consecutive two-fold dilutions over at least 3 log orders of AFGF concentration spanning the complete rise of the response from background through peak DNA synthesis levels. All concentration points were done in quadruplicate on confluent Balb/c 3T3 cells in 96 well dishes. One stimulatory unit was calculated as the amount of AFGF per ml that generated a half-maximal response. The specific mitogenic activity is the number of such stimulatory units per mg of pure AFGF. All samples of AFGF were prediluted to 50 µg/ml in the same TFA/CH₃ CN solvent. The activities of wild-type and mutated AFGF are compared in the following table.

TABLE XIV

| Sample | With Heparin | Without Heparin | Fold Increase |
|---|---|---|---|
| WT | 5.37 ng/ml | 269 pg/ml | 20.0 |

TABLE XIV-continued

| Sample | With Heparin | Without Heparin | Fold Increase |
|---|---|---|---|
| Ser 16 | $(0.186 \times 10^6)$ 33.9 ng/ml | $(3.72 \times 10^6)$ 400 pg/ml | 84.8 |
| Ser 83 | $(0.030 \times 10^6)$ 4.36 ng/ml | $(2.50 \times 10^6)$ 251 pg/ml | 17.4 |
| Ser 117 | $(0.229 \times 10^6)$ 182 ng/ml | $(3.98 \times 10^6)$ 240 pg/ml | 7.58 |
| Ser 16,83 | $(0.549 \times 10^6)$ 800 pg/ml | $(4.17 \times 10^6)$ 195 pg/ml | 4.10 |
| Ser 16,117 | $(1.25 \times 10^6)$ 741 pg/ml | $(5.13 \times 10^6)$ 148 pg/ml | 5.01 |
| Ser 83,117 | $(1.35 \times 10^6)$ 295 pg/ml | $(6.76 \times 10^6)$ 100 pg/ml | 2.95 |
| Ser 16,83,117 | $(3.39 \times 10^6)$ 427 pg/ml $(2.34 \times 10^6)$ | $(10.0 \times 10^6)$ 107 pg/ml $(9.35 \times 10^6)$ | 3.99 |

Figure 2B:
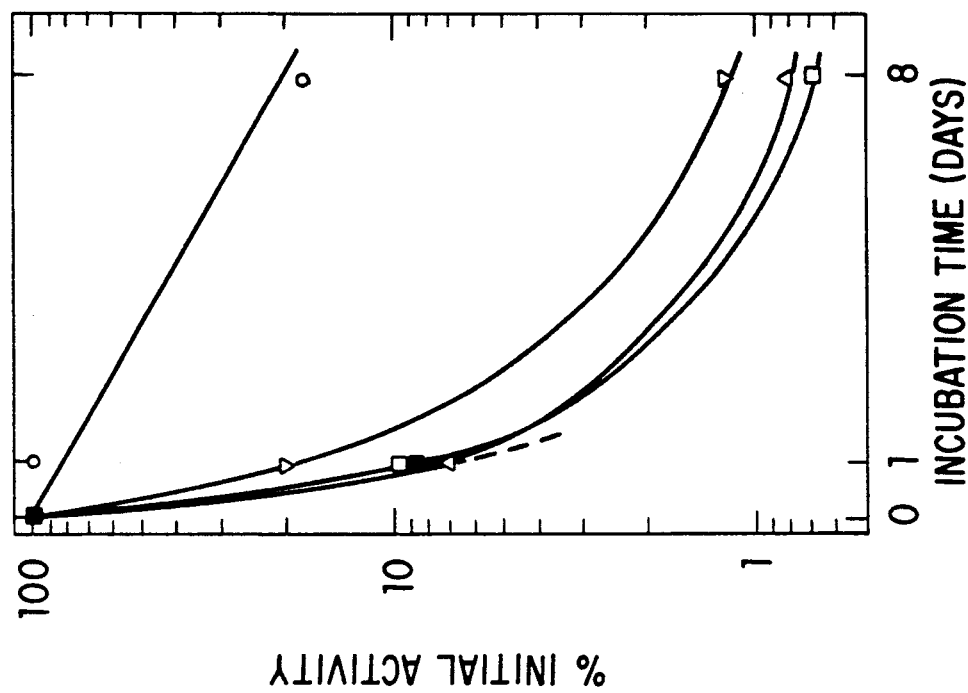
FIG. 2(A) and (B) demonstrate the stability of recombinant wild type haFGF and mutant haFGF measuring mitogenic activity versus time in the presence of heparin (A) and absence of heparin (B).
Figure 2A:
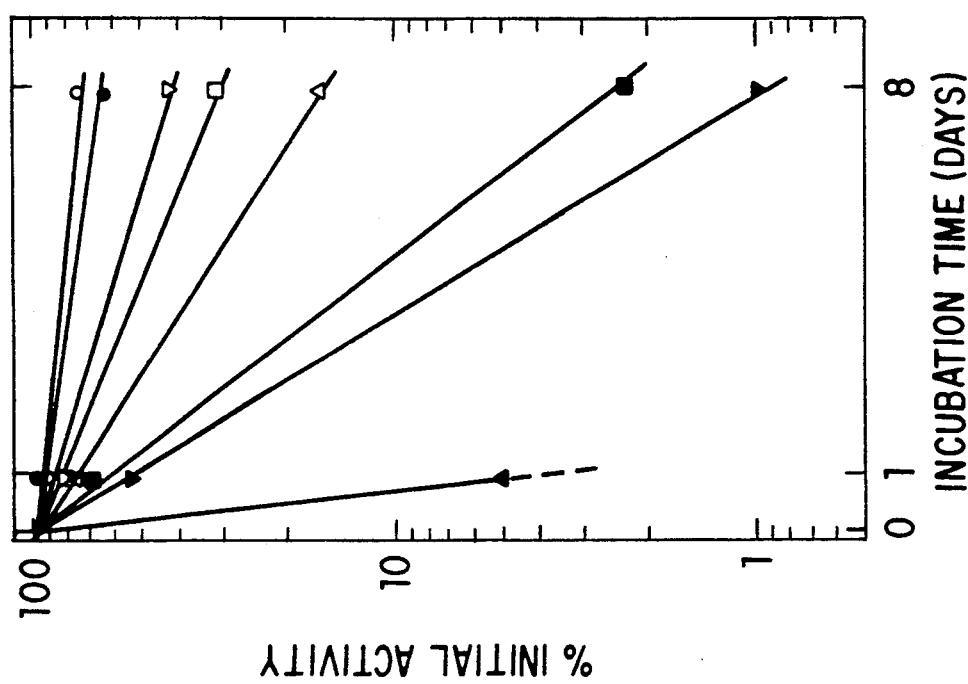

The relative stabilities of the recombinant wild-type haFGF, the single Ser mutants and the multiple Ser mutants were determined. Mitogenic activities were measured following 0, 1 and 8 day incubations in serum-free DME solutions, normally used for serial sample dilutions, that were $CO_2$-buffered to pH 7.3 at 37° C. containing 1 mg/ml human serum albumin. Mitogen samples were stored at 512 ng/ml, with or without 500 μg heparin/ml, equivalent to the 10-fold concentrates from which the highest concentration point in the assay is diluted. Each sample was stored and assayed either in the presence or absence of heparin. The relative stabilities, following scaling to set each day 0 activity to 100%, are shown in FIG. 2 as a function of storage time. In FIG. 2: ▼ corresponds to wild-type; ▲ corresponds to haFGF (Ser 16); ■ corresponds to haFGF (Ser 83); ● corresponds to haFGF (Ser 117); ▽ corresponds to haFGF (Ser 16,83); △ corresponds to haFGF (Ser 16,117); □ corresponds to haFGF (Ser 83,117); and ○ corresponds to haFGF (Ser 16,83,117).

The loss of activity of wild-type haFGF and the mutants in the presence of heparin closely fits an exponential decay, see FIG. 4A. The activities of all the mutants except Ser (16) are more stable than the wild-type mitogen. The most stable mutants, in descending order of stability are Ser 16,83,117), Ser (117) Ser (16,83), Ser (83,117), Ser (16,83) and Ser (83), Ser (16). The stability of Ser (83) was only slightly higher than the wild-type. The various forms of AFGF were less stable in the absence of heparin and with the apparent exception of Ser (16,83,117), the decay-appeared not to be a simple exponential of the time period.

A sample of the expression vector pKK-haFGF(Ser 117) designated A48-lal containing the gene capable of expressing the serine 117 mutant in *E. coli* DH5 was deposited in the American Type Culture Collection, 12301 Parklawn-Drive, Rockville, Mar. 20852 USA, on Sep. 30, 1987 under the Budapest Treaty and has been assigned ATCC number 67522.

What is claimed is:

1. A nucleotide sequence coding for recombinant human mutant microheterogeneous forms of acidic fibroblast growth factor wherein all three cysteine residues at positions 16,83, and 117, numbered in accordance with the native human 140 amino acid microheterogeneous form, are replaced with an amino acid incapable of forming intramolecular or intermolecular disulfide bonds, wherein said mutant acidic fibroblast growth factor has increased biological activity and less dependence on heparin when compared to native acidic fibroblast growth factor and optionally having an additional methionine attached to the N-terminus of said microheterogeneous forms.

2. A nucleotide sequence coding for recombinant human mutant microheterogeneous forms of acidic fibroblast growth factor wherein any two or more of the cysteine residues at positions 16,83 and 177, numbered in accordance with the nativehuman microheterogeneous form, are replaced with an amino acid incapable of forming intramolecular or intermolecular disulfide bonds, wherein said mutant acidic fibroblast growth factor has increased biological activity and less dependence on heparin when compared to native acidic fibroblast growth factor and optionally having an additional methionine attached to the N-terminus of said microheterogeneous forms.

3. A nucleotide sequence coding for recombinant human mutant microheterogeneous forms of acidic fibroblast growth factor wherein the cysteine at position 117, numbered in accordance with the native human 140 amino acid microheterogeneous form, is replaced with an amino acid incapable of forming intramolecular or intermolecular disulfide bonds, and optionally having an additional methionine attached to the N-terminus and wherein said mutant acidic fibroblast growth factor has greater biological activity in the absence of heparin that the native human acidic fibroblast growth factor.

4. A nucleotide sequence coding for recombinant human mutant microheterogeneous forms of acidic fibroblast growth factor of claims 1, 2 or 3 wherein the methionine residue at position 67, numbered in accordance with the native human 140 amino ac id microheterogeneous form, is replaced by a non-air-oxidizable amino acid and optionally having an additional methionine attached to the N-terminus of said microheterogeneous forms wherein said mutant acid fibroblast growth factor has greater biological activity in the absence of heparin than the native human acidic fibroblast growth factor.

* * * * *